US006001595A

United States Patent [19]
Ilmén et al.

[11] Patent Number: 6,001,595
[45] Date of Patent: Dec. 14, 1999

[54] PROMOTERS AND USES THEREOF

[75] Inventors: Marja Ilmén; Maija-Leena Onnela; Merja Penttilä, all of Helsinki, Finland

[73] Assignee: Röhm Enzyme GmbH, Darmstadt, Germany

[21] Appl. No.: 09/066,597

[22] Filed: Apr. 27, 1998

Related U.S. Application Data

[63] Continuation-in-part of application No. 08/980,061, Nov. 26, 1997, and a continuation-in-part of application No. PCT/FI97/00742, Dec. 1, 1997.
[60] Provisional application No. 60/032,156, Nov. 29, 1996, provisional application No. 60/032,959, Dec. 13, 1996, and provisional application No. 60/040,140, Mar. 10, 1997.

[51] Int. Cl.$^6$ ..................................................... C12P 21/02
[52] U.S. Cl. ................. 435/69.1; 435/254.6; 435/320.1; 536/24.1
[58] Field of Search ........................ 536/24.1; 435/320.1, 435/69.1, 252.33, 254.21, 254.11, 254.6

[56] References Cited

FOREIGN PATENT DOCUMENTS

| | | |
|---|---|---|
| 0 137 280 | 4/1985 | European Pat. Off. . |
| WO 85/04672 | 10/1985 | WIPO . |
| WO 93/24621 | 12/1993 | WIPO . |
| WO 94/04673 | 3/1994 | WIPO . |
| WO 98/23642 | 6/1998 | WIPO . |
| WO 98/23764 | 6/1998 | WIPO . |

OTHER PUBLICATIONS

Keränen et al, *Curr. Opinions Biotech.*, vol. 6, Oct. 1995.
Abrahão–Neto, J., et al., "Mitochondrial Functions Mediate Cellulase Gene Expression in *Trichoderma reesei*," *Biochem.* 34:10456–10462 (Aug. 1995).
Bisaria, V.S. and S. Mishra, "Regulatory Aspects of Cellulase Biosynthesis and Secretion," *CRC Crit. Rev. Biotech.* 9:61–103 (1989).
Bissett, J., "A revision of the genus Trichoderma. I. Section Longibrachiatum sect. nov.," *Canadian J. Botany* 62:924–931 (1984).
Cheng, C., et al., "Nucleotide sequence of the cellobiohydrolase gene from *Trichoderma viride*," *Nucleic Acids Res.* 18:5559 (1990).
Chen, C.M., et al., "Nucleotide Sequence and Deduced Primary Structure of Cellobiohydrolase II from *TricHoderma reesei*," *Bio/Technology* 5:274–278 (1987).
El–Gogary, S., et al., "Mechanism by which cellulose triggers cellobiohydrolase I gene expression in *Trichoderma reesei*," *Proc. Natl. Acad. Sci. USA* 86:6138–6141 (1989).
Fowler, T., et al., "Regulation of the cellulase genes of *Trichoderma reesei*," *Proc. of the 2$^{nd}$ Tricel Symposium on Trichoderma reesei Cellulases and other Hydrolases*, Espoo, Finland, P. Suominen and T. Reinkainen, eds., Foundation for Biotechnical and Industrial Fermentation Research 8, pp. 199–210 (1993).
Goldman, G.H., et al., "Sequence of the *Trichoderma viride* phosphoglycerate kinase gene," *Nucleic Acids Research* 18:6717 (1990).

Gritzali, M. and R.D. Brown, Jr., "The Cellulase System of Trichoderma," in: *Hydrolysis of Cellulose: Mechanisms of Enzymatic and Acid Catalysis*, R.D. Brown, Jr. and L. Jurasek, eds., American Chemical Society, Washington D.C., pp. 237–260 (1979).
Herrera–Estrella, A., et al., "High–efficiency transformation system for the biocontrol agents, Trichoderma spp.," *Mol. Microbiol.* 4:839–843 (1990).
Keränen, S. and M. Penttilä, "Production of recombinant proteins in the filamentous fungus *Trichoderma reesei*," *Current Opinion in Biotech.* 6:534–537 (Oct. 1995).
Kirk, T.K., "Biochemistry of Lignin Degradation by *Phanerochaet Chrysosporiu*," in: *Biochemistry and Genetics of Cellulose Degradation*, J.P. Aubert, et al., eds., Academic Press, New York, pp. 315–332 (1988).
Kubicek, C.P., "From Cellulose to Cellulase Inducers: Facts and Fiction," *Proc. of the 2$^{nd}$ Tricel Symposium on Trichoderma reesei Cellulases and other Hydrolases*, Espoo, Finland, P. Suominen and T. Reinikainen, eds., Foundation for Biotechnical and Industrial Fermentation Research 8, pp. 181–188 (1993).
Loewenberg, J.R., "Sophorose induction of an intracellular b–glucosidase in Trichoderma," *Arch. Microbiol.* 137:53–57 (1984).
Mackenzie, D.A., et al., "Regulation of secreted protein production by *filamentous fungi*: recent developments and perspectives," *J. General Microbiol.* 139:2295–2307 (1993).
Meyer, W., et al., "The use of DNA–fingerprint analysis in the classification of some species of the Trichoderma aggregate," *Current Genetics* 21:27–30 (1992).
Morawetz, R., et al., "Presence, transcription and translation of cellobiohydrolase genes in several Trichoderma species," *Current Genetics* 21:31–36 (1992).
O'Donnell, K. and S.W. Peterson, "Isolation, Preservation, and Taxonomy," in: *Biotechnology of Filamentous Fungi: Technology and Products*, D.B. Finkelstein and C. Ball, eds., Butterworth–Heinemann, Boston, MA., pp. 7–39 (1992).
Paloheimo, M., et al., "Enzyme production by *Trichoderma reesei* using the cbh1 promoter," *Proc. of the 2$^{nd}$ Tricel Symposium on Trichoderma reesei Cellulases and other Hydrolases*, Espoo, Finland, P. Suominen and T. Reinikainen, eds., Foundation for Biotechnical and Industrial Fermentation Research 8, pp. 229–238 (1993).

(List continued on next page.)

Primary Examiner—James Ketter
Attorney, Agent, or Firm—Sterne, Kessler, Goldstein & Fox P.L.L.C.

[57] ABSTRACT

Shortened sophorose inducible promoters are provided. The invention further provides vectors containing such promoters hosts transformed with the same, and methods utilizing such promoters for the expression of operably linked sequences.

26 Claims, 5 Drawing Sheets

OTHER PUBLICATIONS

Penttilä, M., et al., "Homology between cellulase genes of *Trichoderma reesei*: complete nucleotide sequence of the endoglucanase I gene," *Gene* 45:253–263 (1986).

Penttilä, M., et al., "Regulation of the expression of Trichoderma cellulase at mRNA and promoter level," *Proc. of the 2nd Tricel Symposium on Trichoderma reesei Cellulases and other Hydrolases*, Espoo, Finland, P. Suominen and T. Reinikainen, eds., Foundation for Biotechnical and Industrial Fermentation Research 8, pp. 189–197 (1993).

Raguz, S., et al., "Isolation and characterization of a cellulose–growth–specific gene from *Agaricus bisporus*," *Gene* 119:183–190 (1992).

Saloheimo, M., et al., "EGIII, a new endoglucanase from *Trichoderma reesei*: the characterization of both gene and enzyme ," *Gene* 63:11–21 (1988).

Saloheimo, M., et al., "A lignin peroxidase–encoding cDNA from the white–rot fungus *Phlebia radiata*: characterization and expression in *Trichoderma reesei*," *Gene* 85:343–351 (1989).

Shoemaker, S., et al., "Molecular Cloning of Exo–Cellobiohydrolase I Derived from *Trichoderma reesei* Strain L27," *Bio/Technology* 1:691–696 (1983).

Strangl, H., et al., "Characterization of the *Trichoderma reesei* cbh2 promoter," *Current Genetics* 23:115–122 (1993).

Teeri, T., et al., "The Molecular Cloning of the Major Cellulase Gene from *Trichoderma reesei*," *Bio/Tecchnology* 1:696–699 (1983).

Teeri, T., et al., "Structure, Function, and Genetics of Cellulases," in:*Biotechnology of Filamentous Fungi: Technology and Products*, D.B. Finkelstein and C. Ball, eds., Butterworth–Heinmann, Boston, MA., pp. 417–445 (1992).

Tenkanen, M. and K. Poutanen, "Significance of esterases in the degradation of xylans," in:*Xylans and Xylanases*, J. Visser, et al., eds., Elsevier, Amsterdam, pp. 203–212 (1992). Tenkanen, M., et al., "Two main xylanases of *Trichoderma reesei* and their use in pulp processing," in: *Xylans and Xylanases*, J. Visser, et al., eds., Elsevier, Amsterdam, pp. 547–550 (1992).

Vaheri, M., et al., "Transglycosylation Products of Cellulase System of *Trichoderma reesei*," *Biotechnology Letters* 1:41–46 (1979).

Van Arsdell, J.N., et al., "Cloning, Charaterization, and Expression in *Saccharomyces cerevisiae* of Endoglucanase I from *Trichoderma reesei*," *Bio/Technology* 5:60–64 (1987).

Wey, T.T., et al., "Molecular Cloning and Sequence Analysis of the Cellobiohydrolase I Gene from *Trichoderma koningii* G39," *Current Microbiol.* 28:31–39 (1994).

Yagüe, E., et al., "Regulation of transcription of the cell gene in *Agaricus bisporus*," *Mol. Microbiol.* 12:41–47 (1994).

Henrique–Silva, F. et al., "Two Regulatory Regions Controlling Basal and Cellulase–Induced Expression of the Gene Encoding Cellobiohydrolase I of *Trichoderma reesei* Are Adjacent to Its TATA Box," *Biochem. Biophys. Res. Commun.* 228:229–237 ( Nov. 12, 1996).

Ilmén, M. et al., "Functional Analysis of the Cellobiohydrolase I Promoter of the Filamentous Fungus *Trichoderma reeseei*," *Mol. Gen. Genet.* 252:303–314 (Dec. 13, 1996).

International Search Report for International Application No. PCT/FI97/00742, Swedish Patent Office, Box 5055, S–102 42 Stockholm (Mar. 12, 1998).

PCT International Preliminary Examination Report for International Application No. PCT/FI97/00742, Swedish Patent Office, Box 5055, S–102 42 Stockholm (Mar. 24, 1999).

|     | 10 | 20 | 30 | 40 | 50 |
|-----|----|----|----|----|----|

```
    1 GAATTCTCACGGTGAATGTAGGCCTTTTGTAGGGTAGGAATTGTCACTCA
   51 AGCACCCCCAACCTCCATTACGCCTCCCCCATAGAGTTCCCAATCAGTGA
  101 GTCATGGCACTGTTCTCAAATAGATTGGGGAGAAGTTGACTTCCGCCCAG
  151 AGCTGAAGGTCGCACAACCGCATGATATAGGGTCGGCAACGGCAAAAAG
  201 CACGTGGCTCACCGAAAAGCAAGATGTTTGCGATCTAACATCCAGGAACC
  251 TGGATACATCCATCATCACGCACGACCACTTTGATCTGCTGGTAAACTCG
  301 TATTCGCCCTAAACCGAAGTGCGTGGTAAATCTACACGTGGGCCCCTTTC
  351 GGTATACTGCGTGTGTCTTCTCTAGGTGGCATTCTTTTCCCTTCCTCTAG
  401 TGTTGAATTGTTTGTGTTGGAGTCCGAGCTGTAACTACCTCTGAATCTCT
  451 GGAGAATGGTGGACTAACGACTACCGTGCACCTGCATCATGTATATAATA
  501 GTGATCCTGAGAAGGGGGGTTTGGAGCAATGTGGGACTTTGATGGTCATC
  551 AAACAAAGAACGAAGACGCCTCTTTTGCAAAGTTTTGTTTCGGCTACGGT
  601 GAAGAACTGGATACTTGTTGTGTCTTCTGTGTATTTTGTGGCAACAAGA
  651 GGCCAGAGACAATCTATTCAAACACCAAGCTTGCTCTTTTGAGCTACAAG
  701 AACCTGTGGGGTATATATCTAGAGTTGTGAAGTCGGTAATCCCGCTGTAT
  751 AGTAATACGAGTCGCATCTAAATACTCCGAAGCTGCTGCGAACCCGGAGA
  801 ATCGAGATGTGCTGGAAAGCTTCTAGCGAGCGGCTAAATTAGCATGAAAG
  851 GCTATGAGAAATTCTGGAGACGGCTTGTTGAATCATGGCGTTCCATTCTT
  901 CGACAAGCAAAGCGTTCCGTCGCAGTAGCAGGCACTCATTCCCGAAAAA
  951 CTCGGAGATTCCTAAGTAGCGATGGAACCGGAATAATATAATAGGCAATA
 1001 CATTGAGTTGCCTCGACGGTTGCAATGCAGGGGTACTGAGCTTGGACATA
 1051 ACTGTTCCGTACCCCACCTCTTCTCAACCTTTGGCGTTTCCCTGATTCAG
 1101 CGTACCCGTACAAGTCGTAATCACTATTAACCCAGACTGACCGGACGTGT
 1151 TTTGCCCTTCATTTGGAGAAATAATGTCATTGCGATGTGTAATTTGCCTG
 1201 CTTGACCGACTGGGGCTGTTCGAAGCCCGAATGTAGGATTGTTATCCGAA
 1251 CTCTGCTCGTAGAGGCATGTTGTGAATCTGTGTCGGGCAGGACACGCCTC
```

FIG. 1A

1301 GAAGGTTCACGGCAAGGGAAACCACCGATAGCAGTGTCTAGTAGCAACCT
1351 GTAAAGCCGCAATGCAGCATCACTGGAAAATACAAACCAATGGCTAAAAG
1401 TACATAAGTTAATGCCTAAAGAAGTCATATACCAGCGGCTAATAATTGTA
1451 CAATCAAGTGGCTAAACGTACCGTAATTTGCCAACGGCTTGTGGGGTTGC
1501 AGAAGCAACGGCAAAGCCCCACTTCCCCACGTTTGTTTCTTCACTCAGTC
1551 CAATCTCAGCTGGTGATCCCCAATTGGGTCGCTTGTTTGTTCCGGTGAA
1601 GTGAAAGAAGACAGAGGTAAGAATGTCTGACTCGGAGCGTTTTGCATACA
1651 ACCAAGGGCAGTGATGGAAGACAGTGAAATGTTGACATTCAAGGAGTATT
1701 TAGCCAGGGATGCTTGAGTGTATCGTGTAAGGAGGTTTGTCTGCCGATAC
1751 GACGAATACTGTATAGTCACTTCTGATGAAGTGGTCCATATTGAAATGTA
1801 AGTCGGCACTGAACAGGCAAAAGATTGAGTTGAAACTGCCTAAGATCTCG
1851 GGCCCTCGGGCCTTCGGCCTTTGGGTGTACATGTTTGTGCTCCGGGCAAA
1901 TGCAAAGTGTGGTAGGATCGAACACACTGCTGCCTTTACCAAGCAGCTGA
1951 GGGTATGTGATAGGCAAATGTTCAGGGGCCACTGCATGGTTTCGAATAGA
2001 AAGAGAAGCTTAGCCAAGAACAATAGCCGATAAAGATAGCCTCATTAAAC
2051 GGAATGAGCTAGTAGGCAAAGTCAGCGAATGTGTATATATAAAGGTTCGA
2101 GGTCCGTGCCTCCCTCATGCTCTCCCCATCTACTCATCAACTCAGATCCT
2151 CCAGGAGACTTGTACACCATCTTTTGAGGCACAGAAACCCAATAGTCAAC
2201 CGCGGACTGCGCATCATG

Total number of bases is: 2218.
DNA sequence composition:  600 A;  501 C;  550 G;  567 T;
Sequence name: ALLC1P

FIG. 1B

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
      (A) LENGTH: 2218 base pairs
      (B) TYPE: nucleic acid
      (C) STRANDEDNESS: both
      (D) TOPOLOGY: linear (ii) MOLECULE TYPE: DNA (genomic)

(xi) SEQUENCE DESCRIPTION: SEQ ID NO: 1:

```
GAATTCTCAC GGTGAATGTA GGCCTTTTGT AGGGTAGGAA TTGTCACTCA AGCACCCCCA    60
ACCTCCATTA CGCCTCCCCC ATAGAGTTCC CAATCAGTGA GTCATGGCAC TGTTCTCAAA   120
TAGATTGGGG AGAAGTTGAC TTCCGCCCAG AGCTGAAGGT CGCACAACCG CATGATATAG   180
GGTCGGCAAC GGCAAAAAAG CACGTGGCTC ACCGAAAAGC AAGATGTTTG CGATCTAACA   240
TCCAGGAACC TGGATACATC CATCATACG CACGACCACT TGATCTGCT GGTAAACTCG    300
TATTCGCCCT AAACCGAAGT GCGTGGTAAA TCTACACGTG GGCCCCTTTC GGTATACTGC   360
GTGTGTCTTC TCTAGGTGGC ATTCTTTTCC CTTCCTCTAG TGTTGAATTG TTTGTGTTGG   420
AGTCCGAGCT GTAACTACCT CTGAATCTCT GGAGAATGGT GGACTAACGA CTACCGTGCA   480
CCTGCATCAT GTATATAATA GTGATCCTGA AAGGGGGGT TTGGAGCAAT GTGGGACTTT    540
GATGGTCATC AAACAAAGAA CGAAGACGCC TCTTTTGCAA AGTTTTGTTT CGGCTACGGT   600
GAAGAACTGG ATACTTGTTG TGTCTTCTGT GTATTTTTGT GGCAACAAGA GGCCAGAGAC   660
AATCTATTCA AACACCAAGC TTGCTCTTTT GAGCTACAAG AACCTGTGGG GTATATATCT   720
AGAGTTGTGA AGTCGGTAAT CCCGCTGTAT AGTAATACGA GTCGCATCTA AATACTCCGA   780
AGCTGCTGCG AACCCGGAGA ATCGAGATGT GCTGGAAAGC TTCTAGCGAG CGGCTAAATT   840
AGCATGAAAG GCTATGAGAA ATTCTGGAGA CGGCTTGTTG AATCATGGCG TTCCATTCTT   900
CGACAAGCAA AGCGTTCCGT CGCAGTAGCA GGCACTCATT CCCGAAAAAA CTCGGAGATT   960
CCTAAGTAGC GATGGAACCG AATAATATA ATAGGCAATA CATTGAGTTG CCTCGACGGT  1020
TGCAATGCAG GGGTACTGAG CTTGGACATA ACTGTTCCGT ACCCCACCTC TTCTCAACCT  1080
TTGGCGTTTC CCTGATTCAG CGTACCCGTA CAAGTCGTAA TCACTATTAA CCCAGACTGA  1140
CCGGACGTGT TTTGCCCTTC ATTTGGAGAA ATAATGTCAT TGCGATGTGT AATTTGCCTG  1200
CTTGACCGAC TGGGGCTGTT CGAAGCCCGA ATGTAGGATT GTTATCCGAA CTCTGCTCGT  1260
AGAGGCATGT TGTGAATCTG TGTCGGGCAG GACACGCCTC GAAGGTTCAC GGCAAGGGAA  1320
ACCACCGATA GCAGTGTCTA GTAGCAACCT GTAAAGCCGC AATGCAGCAT CACTGGAAAA  1380
TACAAACCAA TGGCTAAAAG TACATAAGTT AATGCCTAAA GAAGTCATAT ACCAGCGGCT  1440
AATAATTGTA CAATCAAGTG GCTAAACGTA CCGTAATTTG CCAACGGCTT GTGGGGTTGC  1500
AGAAGCAACG GCAAAGCCCC ACTTCCCCAC GTTTGTTTCT TCACTCAGTC AATCTCAGC   1560
TGGTGATCCC CCAATTGGGT CGCTTGTTTG TTCCGGTGAA GTGAAAGAAG ACAGAGGTAA  1620
GAATGTCTGA CTCGGAGCGT TTTGCATACA ACCAAGGGCA GTGATGGAAG ACAGTGAAAT  1680
GTTGACATTC AAGGAGTATT TAGCCAGGGA TGCTTGAGTG TATCGTGTAA GGAGGTTTGT  1740
CTGCCGATAC GACGAATACT GTATAGTCAC TTCTGATGAA GTGGTCCATA TTGAAATGTA  1800
AGTCGGCACT GAACAGGCAA AAGATTGAGT TGAAACTGCC TAAGATCTCG GCCCTCGGG   1860
CCTTCGGCCT TTGGGTGTAC ATGTTTGTGC TCCGGGCAAA TGCAAAGTGT GGTAGGATCG  1920
AACACACTGC TGCCTTTACC AAGCAGCTGA GGGTATGTGA TAGGCAAATG TTCAGGGGCC  1980
ACTGCATGGT TTCGAATAGA AAGAGAAGCT TAGCCAAGAA CAATAGCCGA TAAAGATAGC  2040
CTCATTAAAC GGAATGAGCT AGTAGGCAAA GTCAGCGAAT GTGTATATAT AAAGGTTCGA  2100
GGTCCGTGCC TCCCTCATGC TCTCCCCATC TACTCATCAA CTCAGATCCT CCAGGAGACT  2160
TGTACACCAT CTTTTGAGGC ACAGAAACCC AATAGTCAAC CGCGGACTGC GCATCATG    2218
```

(2) INFORMATION FOR SEQ ID NO: 2:

(i) SEQUENCE CHARACTERISTICS:
        (A) LENGTH: 29 base pairs
        (B) TYPE: nucleic acid

```
        (C) STRANDEDNESS: both
        (D) TOPOLOGY: linear (ii) MOLECULE TYPE: DNA (genomic)

(xi) SEQUENCE DESCRIPTION: SEQ ID NO: 2:

TGAGCTAGTA GGCAAAGTCA GCGAATGTG                                          29

(2) INFORMATION FOR SEQ ID NO: 3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "PCR primer"

(xi) SEQUENCE DESCRIPTION: SEQ ID NO: 3:

GGGAATTCAT GATGCGCAGT CCGCGG                                             26

(2) INFORMATION FOR SEQ ID NO: 4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "PCR primer"

(xi) SEQUENCE DESCRIPTION: SEQ ID NO: 4:

GGGAATTCGG TCACCAAAGA TAGCCTCATT AAACGG                                  36

(2) INFORMATION FOR SEQ ID NO: 5:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "PCR primer"

(xi) SEQUENCE DESCRIPTION: SEQ ID NO: 5:

GGGAATTCGG TCACCTGAGC TAGTAGGCAA AGTCAGC                                 37

(2) INFORMATION FOR SEQ ID NO: 6:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "PCR primer"

(xi) SEQUENCE DESCRIPTION: SEQ ID NO: 6:

GGGAATTCGG TCACCGAATG TGTATATATA AAGGTTCG                                38

(2) INFORMATION FOR SEQ ID NO: 7:

(i) SEQUENCE CHARACTERISTICS:
        (A) LENGTH: 40 base pairs
        (B) TYPE: nucleic acid
```

```
        (C) STRANDEDNESS: both
        (D) TOPOLOGY: linear (ii) MOLECULE TYPE: DNA (genomic)

(xi) SEQUENCE DESCRIPTION: SEQ ID NO: 7:

TGAGCTAGTA GGCAAAGTCA GCGAATGTGT ATATATAAAA                              40

(2) INFORMATION FOR SEQ ID NO: 8:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "oligonucleotide"

(xi) SEQUENCE DESCRIPTION: SEQ ID NO: 8:

GATCCTGAGC TAGTAGGCAA AGTCAGCGAA TGTGTGAGCT AGTAGGCAAA GTCAGCGAAT         60

GTGTGAGCTA GTAGGCAAAG TCAGCGAATG TGG                                     93

(2) INFORMATION FOR SEQ ID NO: 9:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "oligonucleotide"

(xi) SEQUENCE DESCRIPTION: SEQ ID NO: 9:

GATCCCACAT TCGCTGACTT TGCCTACTAG CTCACACATT CGCTGACTTT GCCTACTAGC         60

TCACACATTC GCTGACTTTG CCTACTAGCT CAG                                     93

(2) INFORMATION FOR SEQ ID NO: 10:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "oligonucleotide"

(xi) SEQUENCE DESCRIPTION: SEQ ID NO: 10:

GATCCTGAAG AATGGGAAGC ATTGCTAAGC GGTGTGAAGA ATGGGAAGCA TTGCTAAGCG         60

GTGTGAAGAA TGGGAAGCAT TGCTAAGCGG TGG                                     93

(2) INFORMATION FOR SEQ ID NO: 11:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "oligonucleotide"

(xi) SEQUENCE DESCRIPTION: SEQ ID NO: 11:

GATCCCACCG CTTAGCAATG CTTCCCATTC TTCACACCGC TTAGCAATGC TTCCCATTCT         60

TCACACCGCT TAGCAATGCT TCCCATTCTT CAG                                     93
```

(2) INFORMATION FOR SEQ ID NO: 12:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 12:

AATTCATTAA ACGGAATGAG CTAGTAGGCA AAGTCAGCGA ATGTGT      46

(2) INFORMATION FOR SEQ ID NO: 13:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 13:

CTAGACACAT TCGCTGACTT TGCCTACTAG CTCATTCCGT TTAATG      46

(2) INFORMATION FOR SEQ ID NO: 14:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 14:

AATTCGATAA AGATAGCCTC ATTAAACGGA ATGAGCTAGT T      41

(2) INFORMATION FOR SEQ ID NO: 15:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 15:

CTAGAACTAG CTCATTCCGT TTAATGAGGC TATCTTTATC G      41

(2) INFORMATION FOR SEQ ID NO: 16:

(i) SEQUENCE CHARACTERISTICS:
        (A) LENGTH: 184 base pairs
        (B) TYPE: nucleic acid
        (C) STRANDEDNESS: both
        (D) TOPOLOGY: linear (ii) MOLECULE TYPE: DNA (genomic)

(xi) SEQUENCE DESCRIPTION: SEQ ID NO: 16:

```
AAAGATAGCC TCATTAAACG GAATGAGCTA GTAGGCAAAG TCAGCGAATG TGTATATATA        60

AAGGTTCGAG GTCCGTGCCT CCCTCATGCT CTCCCCATCT ACTCATCAAC TCAGATCCTC       120

CAGGAGACTT GTACACCATC TTTTGAGGCA CAGAAACCCA ATAGTCAACC GCGGACTGCG       180

CATC                                                                    184
```

(2) INFORMATION FOR SEQ ID NO: 17:

(i) SEQUENCE CHARACTERISTICS:
        (A) LENGTH: 161 base pairs
        (B) TYPE: nucleic acid
        (C) STRANDEDNESS: both
        (D) TOPOLOGY: linear (ii) MOLECULE TYPE: DNA (genomic)

(xi) SEQUENCE DESCRIPTION: SEQ ID NO: 17:

```
TGAGCTAGTA GGCAAAGTCA GCGAATGTGT ATATATAAAG GTTCGAGGTC CGTGCCTCCC        60

TCATGCTCTC CCCATCTACT CATCAACTCA GATCCTCCAG GAGACTTGTA CACCATCTTT       120

TGAGGCACAG AAACCCAATA GTCAACCGCG GACTGCGCAT C                           161
```

(2) INFORMATION FOR SEQ ID NO: 18:

(i) SEQUENCE CHARACTERISTICS:
        (A) LENGTH: 140 base pairs
        (B) TYPE: nucleic acid
        (C) STRANDEDNESS: both
        (D) TOPOLOGY: linear (ii) MOLECULE TYPE: DNA (genomic)

(xi) SEQUENCE DESCRIPTION: SEQ ID NO: 18:

```
CGAATGTGTA TATATAAAGG TTCGAGGTCC GTGCCTCCCT CATGCTCTCC CCATCTACTC        60

ATCAACTCAG ATCCTCCAGG AGACTTGTAC ACCATCTTTT GAGGCACAGA AACCCAATAG       120

TCAACCGCGG ACTGCGCATC                                                   140
```

(2) INFORMATION FOR SEQ ID NO: 19:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(xi) SEQUENCE DESCRIPTION: SEQ ID NO: 19:

```
AAAGGATCCT TATACATTAT ATAAAGTAAT G                                       31
```

(2) INFORMATION FOR SEQ ID NO: 20:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(xi) SEQUENCE DESCRIPTION: SEQ ID NO: 20:

```
ATATAGTCGA CCTCGGGGAC ACCAAATATG G                                       31
```

(2) INFORMATION FOR SEQ ID NO: 21:

(i) SEQUENCE CHARACTERISTICS:
        (A) LENGTH: 55 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO: 21:

TCTAGTGGCC AGAATGCCTA GGTCACCTCT AGAGGTACCC TGCAGCTCGA GCTAG        55

(2) INFORMATION FOR SEQ ID NO: 22:

(i) SEQUENCE CHARACTERISTICS:
        (A) LENGTH: 37 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO: 22:

CCGCGGACTG CGCATCATGC AGGATCCCGT CGTTTTA        37

(2) INFORMATION FOR SEQ ID NO: 23:

(i) SEQUENCE CHARACTERISTICS:
        (A) LENGTH: 22 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO: 23:

TAATAATAAC CGGCGGTATT GG        22

PROMOTERS AND USES THEREOF

CROSS-REFERENCE TO RELATED APPLICATIONS

The present application is a continuation-in-part of U.S. appl. Ser. No. 08/980,061, filed Nov. 26, 1997, and PCT/FI97/00742, filed Dec. 1, 1997, each of which disclosure is incorporated herein in entirety by reference. Both U.S. appl. Ser. No. 08/980,061 and PCT/FI97/00742 claim benefit of the filing date of U.S. appl. Ser. No. 60/032,156, filed Nov. 29, 1996, U.S. appl. Ser. No. 60/032,959, filed Dec. 13, 1996, and U.S. appl. Ser. No. 60/040,140, filed Mar. 10, 1997, each of which disclosure is also incorporated herein in entirety by reference.

BACKGROUND OF THE INVENTION

Trichoderma reesei is a filamentous fungus able to carry out efficient hydrolysis of crystalline cellulose to glucose through the action of a number of secreted cellulase enzymes. The major secreted protein is cellobiohydrolase I (CBHI) that may constitute up to 60% of the secreted proteins. This amount, derived from the single copy cbh1 gene, corresponds to roughly 25% of all protein synthesized by the fungus in cellulase-inducing growth conditions.

Availability of the carbon source regulates production of CBHI (reviewed in Bisaria, V. S. et al., *CRC Crit. Rev. Biotechnol.* 9: 61–103 (1989)) and the regulation occurs at the level of transcription of the gene encoding CBHI (El-Gogary, S. et al., *Proc. Natl. Acad. Sci. USA* 86: 6138–6141 (1989); Fowler, T. et al., Proceedings of the second TRICEL symposium on *Trichoderma reesei* cellulases and other hydrolases, Espoo, Finland. Suominen P., and Reinikainen T. (eds.), Foundation for Biotechnical and Industrial Fermentation Research 8: 199–210, Helsinki (1993); Kubicek, C. P. et al., Proceedings of the second TRICEL symposium on *Trichoderma reesei* cellulases and other hydrolases, Espoo, Finland. Suominen P, and Reinikainen T (eds.), Foundation for Biotechnical and Industrial Fermentation Research 8: 181–188, Helsinki (1993); Penttilä, M. E. et al., Proceedings of the second TRICEL symposium on *Trichoderma reesei* cellulases and other hydrolases, Espoo, Finland. Suominen, P., and Reinikainen, T. (eds), Foundation for Biotechnical and Industrial Fermentation Research 8: 189–198, Helsinki (1993): Abrahão-Neto, J. et al., *Biochemistry* 34: 10456–10462 (1995)).

cbh1 mRNA has been shown to be several thousand fold more abundant when the fungus is grown on a medium containing cellulose compared with glucose. Use of glucose as a carbon source represses cellulase expression (Penttilä, M. E. et al., Proceedings of the second TRICEL symposium on *Trichoderma reesei* cellulases and other hydrolases, Espoo, Finland. Suominen P, and Reinikainen T (eds. ), Foundation for Biotechnical and Industrial Fermentation Research 8: 189–198, Helsinki (1993)).

Sophorose consists of two glucose units linked by a β-1,2-glycosidic bond. Sophorose has also been considered to be a possible natural inducer formed from β-1,4-linked cello-oligosaccharides such as cellobiose by transglycosylation (Vaheri, M. et al., *Biotechnol Lett.* 1: 41–46 (1979); Gritzali, M. etal., *Adv. Chem. Ser.* 181: 237–260 (1979); Loewenberg, J. R., *Arch. Microbiol.* 137: 53–57 (1984)). Sophorose is known to induce the cbh1 promoter.

Successful production of recombinant proteins of fungal and mammalian origin under the control of the cbh1 promoter has been achieved (reviewed by Paloheimo, M. et al., Proceedings of the second TRICEL symposium on *Trichoderma reesei* cellulases and other hydrolases, Espoo, Finland. Suominen P, and Reinikainen T (eds.), Foundation for Biotechnical and Industrial Fermentation Research 8: 229–238, Helsinki (1993); Keränen, S. et al., *Curr. Opin. Biotechnol.* 6: 534–537 (1995)). Despite biological and biotechnical importance of cellulase production, the specific elements regulating such expression at the transcriptional level are generally unknown. Promoter sequence comparisons carried out for fungal cellulase promoters (Raguz, S. et al., *Gene* 119: 183–190 (1992); Stangl, H. et al., *Curr. Genet.* 23: 115–122 (1993); Yague, E. et al., *Mol. Microbiol.* 12: 41–47 (1994)) have revealed little similarities and the functional significance of this similarity, if any, is unknown. The analysis of the promoter of the cellulase gene cbh2 of *T. reesei* by a preliminary gel shift analysis showed that cellular proteins bind the promoter sequences (Stangl, H. et al., *Curr. Genet.* 23: 115–122 (1993)). However, the function of those proteins, whether they were involved in the regulatory induction of transcription by specific activators or were generally required for the transcriptional process (such as a polymerase), is also unknown.

The cbh1 promoter is contained on a long 2.2 kb piece of *T. reesei* genomic DNA flanked on the 5' end by an EcoRI site and on the 3' end by the start of the CBHI coding sequence. The ability to design recombinant constructs and vectors for the production of a desired sequence under the control of this promoter would be more efficient if it were possible to shorten the promoter but yet retain the ability of the promoter to respond to inducers such as sophorose. This is especially desirable when the vector is a shuttle vector that is to be maintained in a bacterial or yeast host. However, such shortened forms of the cbh1 promoter are unknown.

SUMMARY OF THE INVENTION

This invention is first directed to shortened sophorose inducible cellulase and hemicellulase promoters, and their use to express operably linked proteins in fungal hosts, especially filamentous fungi.

The invention is further directed to DNA sequences or vectors containing such promoters, useful for the transformation of a desired host cell.

The invention is further directed to recombinant hosts transformed with such DNA or vectors, and especially filamentous fungal hosts.

The invention is further directed to recombinant hosts transformed with such DNA or vectors, and with DNA sequences encoding proteins mediating transcriptional regulation through the promoter sequences of this invention.

The invention is further directed to a process for producing a desired protein or antisense RNA of interest and expressing the desired protein or antisense RNA that is operably linked to the shortened promoters of the invention.

BRIEF DESCRIPTION OF THE DRAWINGS

FIG. 1A and B. Sequence of 2218 bases of the wild type *T. reesei* cbh1 promoter that is proximal to the 5' end of the coding sequence.

Figure 3A:
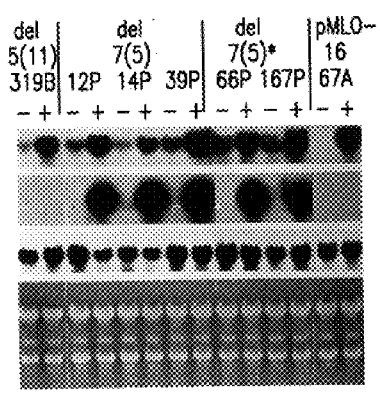
Figure 3B:
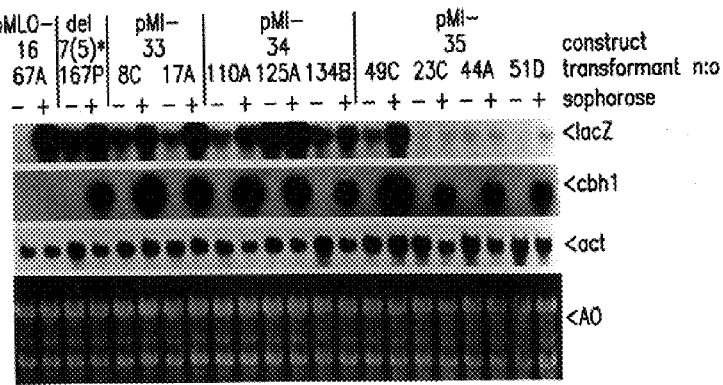

FIG. 3 (A and B). A. Northern analysis of lacZ expression from selected deletion derivatives of the cbh1 promoter of transformants grown on sorbitol medium with (+) or without (−) sophorose addition. The expression cassette del7(5) lacks promoter sequences between nucleotides −1497 to −210 upstream of the translation initiation codon and del7 (5)* lacks all sequences upstream of −210. del5(11) lacks sequences between −1497 and −390 bp. In pMLO16 the wild type cbh1 promoter is joined to lacZ. del5(11) and pMLO16 have the expression cassettes integrated as a single copy at the cbh1 locus and lack the endogenous cbh1. B. Northern analysis on lacZ expression under the shortest deletion derivatives of the cbh1 promoter. pMI-33, pMI-34 and pMI-35 lack all sequences upstream of −184, −161 and −140, respectively. 5 μg RNA was loaded on both gels and the blots were hybridized with the probes indicated. AO, acridine orange stained gel.

Figure 4:
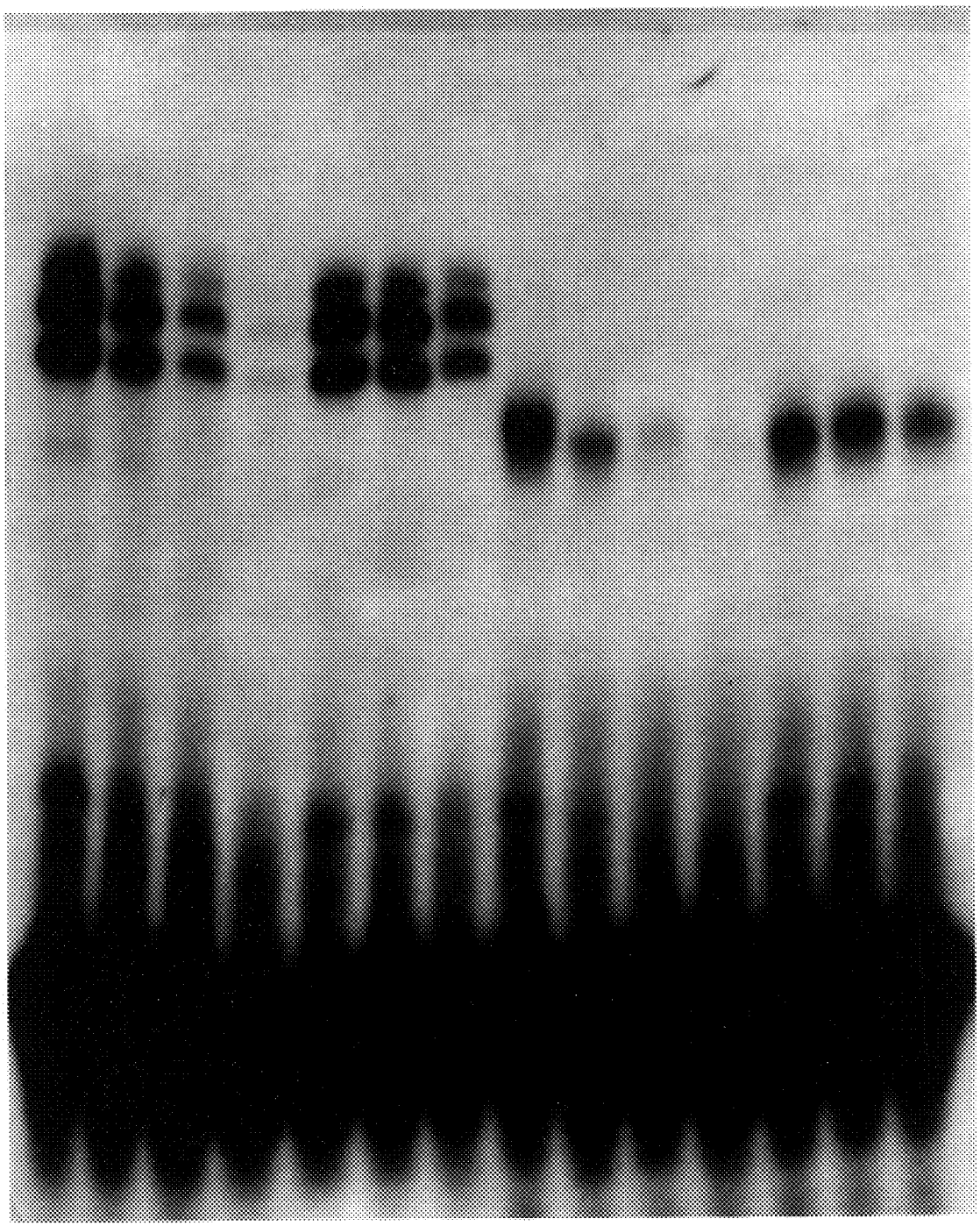

FIG. 4. DNA mobility shift assay visualizing proteins from total protein lysates binding to the cbh1 promoter fragment from −134 to −173. Lanes 1–7, total protein lysate from a glucose grown culture. Lanes 2–4, 5, 50, 100× amounts of specific competitor DNA (same as the labeled promoter fragment). Lanes 5–7, 5, 10, 100× amounts of unspecific competitor DNA. Lanes 8–14, total protein lysate from Avicel cellulose grown culture. Lanes 9–11, same as lanes 2–4, and lanes 12–14, same as lanes 5–7.

DESCRIPTION OF THE DEPOSITS

Plasmid pAS34 is also called VTT-F-97077 and was deposited as VTT-F-97077 at the DSMZ (Deutche Sammlung von Mikroorganismem und Zelkulturen GmbH), Mascheroder Weg 1b, D-38124 Braunschweig, F.R.G. in *E. coli* on Mar. 7, 1997 and assigned accession number DSM 11451.

Plasmid pAS33 is also called VTT-F-97078 and was deposited as VTT-F-97078 at the DSMZ in *E. coli* on Mar. 7, 1997 and assigned accession number DSM 11452.

Plasmid pAS28 is also called VTT-F-97079 and was deposited as VTT-F-97079 at the DSMZ in *E. coli* on Mar. 7, 1997 and assigned accession number DSM 11453.

Plasmid pAS26 is also called VTT-F-97080 and was deposited as VTT-F-97080 at the DSMZ in *E. coli* on Mar. 7, 1997 and assigned accession number DSM 11454.

DETAILED DESCRIPTION OF THE PREFERRED EMBODIMENTS

General principles of the biochemistry and molecular biology of the filamentous fungi are set forth, for example in Finkelstein, D. B. et al., eds., *Biotechnology of Filamentous Fungi. Technology and Products*, Butterworth-Heinemann, publishers, Stoneham, Mass. (1992) and Bennett, J. W. et al., *More Gene Manipulations in Fungi*, Academic Press-liarcourt Brace Jovanovich, publishers, San Diego Calif. (1991).

This invention provides shortened sophorose inducible cellulase and hemicellulase promoters, methods for creating such shortened promoters and methods for their use. Surprisingly, it has been found that cellulase and hemicellulase promoters, such as the cbh1 promoter, can be greatly shortened and still retain the ability to be induced by sophorose.

By a "shortened" promoter is meant a promoter that is truncated on its 5' end (relative to the direction of transcription) when compared to the length of the native promoter. Thus, for example, a promoter that is shortened to remove at least one regulatory element of the native promoter is thus a shortened promoter within the invention. As a further example, in a preferred embodiment, a shortened *T. reesei* cbh1 promoter of the invention that is smaller than the "native" *T. reesei* cbh1 promoter, is one smaller than the 1497 bp sequence (bases −1497 to −1) that is found immediately 5' to the start of the CBHI coding sequence and which is flanked on its 3' end by the CBHI protein coding region. The sequence of the native *T. reesei* cbh1 promoter is known (FIG. 1 [SEQ ID No. 1] and Nakari et al., WO94/04673).

The shortened sophorose inducible promoters of the invention retain the ability to be induced by sophorose. Thus the level of expression of a desired protein of interest can be regulated by the presence or absence of sophorose in the medium.

Other inducers of the shortened cbh1 promoters of the invention include cellobiose or other inducers naturally present in industrial (complex) growth media. Further, in a preferred embodiment, the shortened forms of the cellulase and hemicellulase promoters of the invention lack the glucose repression sites; therefore, in a preferred embodiment, the shortened promoters of the invention are also not repressed by the presence of glucose in the medium.

Surprisingly, it has been found that the native cellulase and hemicellulase promoters can be greatly shortened and retain the ability to express an operably linked gene, even in the absence of their ability to be induced by sophorose. For example, the cbh1 promoter can be shortened to include only 140 bases and still functions to direct the expression of an operably linked gene, albeit at a low level of expression. Therefore, while such promoters are not optimally responsive to sophorose, and may show no response to sophorose, it has been found that the desired cellulase and hemicellulase promoter may be shortened to a length of 140 bases and still be functional.

Preferably, the shortened promoters are of a length such that the strength of the full-length promoter is retained. cbh1 promoters that retain at least 161 bases, or even 184 bases of the sequence that is proximal to the 5' end of the coding sequence, have a higher level of expression than those that contain 140 bases of the sequence that is proximal to the 5' end of the coding sequence, and not only can direct transcription of operably linked sequences in a relatively efficient and strong manner that is not repressed by glucose but also are inducible with sophorose. Longer (but shortened relative to the full-length) promoters are thus possible too. The 5' end of the shortened promoters of the invention may be at any position that is further upstream of position −133 (which is the first position upstream of the TATA site).

Especially useful 5' end points for the shortened promoters of the invention include promoters that end at positions −210, −340, −390, and −500.

Sequences mediating, sophorose induction lie within the 161 bp sequence immediately upstream of (5' to) the initiator ATG in the cbh1 promoter (i.e., proximal to the 5' end of the coding sequence). Thus, the DNA element(s) responsible for sophorose induction is present in the sequence of bases that are found within the sequence at positions −161 to −1 in the native *T. reesei* cbh1 promoter. The sequences mediating sophorose induction are either in the 30 bp region 5' of TATA, or in the region downstream of the TATA-box. These sequences seem to be also responsible for the expression observed on cellobiose medium in the plate assays. Position −133 is the first nucleotide upstream of the TATA sequence. The sequence of the region between −161 and −133 is: 5'TGAGCTAGTAGGCAAAGTCAGCGAATGTG [SEQ ID No.2]. It is this sequence, or a fragment of this sequence that is thought to be responsible for sophorose induction of the cbh1 promoter. The sophorose responsive shortened promoter region can be inserted in multiple copies in a shortened cbh1 promoter so as to maximally enhance induction of gene expression from this promoter. Furthermore, this element can be inserted into other fungal promoters in one or multiple copies to bring these promoters under regulation mediated through this element. These promoters may be natural (native) promoters or engineered ones, for instance promoters that lack binding sites for a glucose repressor or some other transcription factor(s). Simultaneously a transcription activating protein like DNA-binding activator protein recognizing this element can be expressed in the host cell leading to enhanced production of a desired protein product. The organism from which the DNA binding protein and the corresponding target sequence originate can be different from the production host organism.

Sequences needed for glucose repression are found between −500 and −740 in the cbh1 promoter. Removing sequences above (that is, 5' to) −500 and preferably above −210 in the *T. reesei* cbh1 promoter results in a modified promoter that can been induced by sophorose but not repressed by glucose. Modifications that result in glucose derepression are described in Nakari et al., WO94/04673. If desired, to eliminate glucose repression, it is necessary to delete or to mutate the glucose repressor binding sites in the promoter. In the *T. reesei* cbh1 promoter, there are such sites: six have the hexanucleotide sequences 5'-(C/G)TGGGG. The sites are found −691, −699, −725, −1006, −1154 and −1510 bases upstream of the protein coding region (i.e., positions −691, −699, −725, −1006, −1154 and −1510 of the cbh1 promoter). Therefore, for example, to provide a promoter that is less responsive to glucose, the 5' end of the chb1 promoter is truncated anywhere between approximately position −500 to position −210 from the start of the coding sequence, and the resulting promoter still retains the ability to be induced by sophorose.

Shortened forms of other cellulase or hemicellulase promoters that are responsive to sophorose may be made and used as described for the shortened cbh1 promoter exemplified herein, either by shortening the native promoter or by shortening and/or modifying the native promoter to include SEQ ID No. 2. Therefore, the invention includes cellulase or hemicellulase promoters that are shortened according to the guidance provided for the exemplified cbh1 promoter, and thus that retain the ability to be induced by sophorose.

In a preferred embodiment, the shortened promoter is a shortened cellulase promoter, and in a highly preferred embodiment, it is a shortened cbh1, cbh2, egl1, egl2 or egl5 promoter. In an especially preferred embodiment, the shortened promoter is a shortened cbh1 promoter.

In a further preferred embodiment, the shortened cellulase or hemicellulase sophorose inducible promoter of the invention is a shortened cellulase or hemicellulase promoter of any member of the Trichoderma species, and in particular, promoters of *T. reesei*, *T. harzianum*, *T. longibrachiatum*, *T. viride*, and *T. koningii*. In an especially preferred embodiment, the species from which the shortened promoter is derived is *T. reesei*. Further, in another especially preferred embodiment, the promoter from which the shortened promoter is derived is the native *T. reesei* cbh1, cbh2, egl1, egl2 or egl5 promoter. Thus, examples of cbh1 and cbh2 promoters from Trichoderma that are known and could be shortened according to the invention include the *T. koningii* cbh1 promoter (Wey, T. T. et al., *Curr. Microbiol.* 28: 31–39 (1994)), the *T. reesei* cbh2 promoter (Stangl, H. et al., *Curr. Genet.* 23: 115–122 (1993)), and the *T. viride* cbh1 promoter (Cheng, C. et al., *Nucl. Acids Res.* 18: 5559 (1990)).

Those skilled in the art will recognize that the absolute nucleotide base boundaries discussed above are not generally definitive of the promoter activity (unless otherwise noted) but rather that, as is common in such sequences, one or more bases can be added or subtracted from the sequence without altering its ability to function as expected.

A method for cloning genes activating expression through a specific promoter can be based on expression of a complete cDNA library from the desired organism, in a second host, for example, in the yeast *S. cerevisiae*. The second host, for example, the yeast strain, is first transformed with a reporter construct in which expression of a reporter gene is under the control of (operably linked to) a desired heterologous (or homologous) promoter thought to contain a binding site of (or is at least responsive to) the transcriptional regulatory protein in question. This could be a promoter for which regulatory features (such as inducers, repressors, growth conditions that turn it on and off, etc) are known but for which the actual regulatory proteins are not known or at least the corresponding genes are not cloned. Also, this could be a promoter for which no known inducers or regulatory mechanisms have yet been identified.

The second strain, such as, for example, the yeast strain discussed above, is then transformed with a sample from a cDNA bank that is to be screened for the presence of genes capable of expressing proteins that activate the promoter that is operably linked to the reporter gene. This may be a cDNA bank that is from the same organism as that of the promoter or from a different organism. Preferably, the clones in the cDNA bank are in the form of an expression library wherein expression of proteins encoded by the clones is provided in a constitutive or inducible manner. The design of the expression library should be such that promoters operably linked to the cDNA constructs are capable of functioning in the organism.

When the second host described above contains both a clone (from the expression library) that expresses a transcriptional activator that is capable of regulating the promoter that is operably linked to the reporter construct, and also the host contains the reporter construct, expression of the reporter should be such that induction of the reporter's promoter's expression occurs only when activators of the gene are present. Alternatively, the presence of the activator can be identified as an increase in the expression of the reporter gene over a base level that is found in the absence of the activator.

A useful reporter sequence to identify transcriptional activator proteins when *S. cerevisiae* is the host is the HIS3 gene. *S. cerevisiae* host strains (his3-minus) are available where the HIS3 gene has been deleted or otherwise inactivated in a way that they cannot grow without added histidine unless the yeast has been transformed with a functional HIS3 gene. Consequently, by transforming such hosts with a HIS3 DNA construct to which a desired promoter has been operably linked and also transforming such hosts with the gene bank from which activator genes are to be identified, yeast clones harboring the desired activator gene can be found based on their ability to grow without histidine addition to the medium.

Using yeast genetic methods, the ability of the activator to activate only in the presence of the specific promoter can be confirmed. Possibly leakiness of the reporter construct can be avoided, when necessary, by placing a stuffer fragment in between the upstream vector sequences and the promoter, or alternatively, for example, by using appropriate amounts of the competitive inhibitor of the HIS3 gene product, aminotriatzole (for example, 1–100 mM), in the medium.

The TATA region on the reporter gene's promoter can be provided from the desired reporter gene, for example, the HIS3 gene, or alternatively from the promoter of question. The reporter gene can be also any other gene for which the desired result, activation or repression, can be detected in a similar manner. Furthermore, it can, for instance, encode beta-galactosidase as described for many reporter systems, or it can be, for example, CUPI or an antibiotic resistance marker such as G418 and its activity detected based on the copper or antibiotics resistance, respectively, that it confers to the yeast harboring the activator clone.

The advantage of the method is that no previous knowledge of the identity or presence of the transcriptional regulatory protein, such as the activator, or of the protein's binding site is needed. Unlike many other methods, large promoter fragments can be operably linked to the reporter gene. However, the method works also for smaller fragments of the promoter, and once the activator has been cloned, its binding sites in the promoter can be mapped by replacing the whole promoter by overlapping smaller fragments of the same. Furthermore, the method can also be used to test whether promoters or promoter fragments contain binding sites for certain activators.

A yeast-based system is especially useful for cloning of fungal activator genes regulating genes encoding filamentous fungal extracellular enzymes since the yeast S. cerevisiae does not generally produce such enzymes or transcriptional regulatory proteins responsible for their production, S. cerevisiae being an exception amongst yeasts and filamentous fungi. Thus it is unlikely that proteins native to the yeast host would activate the reporter construct causing background.

In a similar manner, transcriptional activator proteins that regulate the transcription of themselves or of other transcriptional activator proteins can be identified, using the same reporter system as described above. The host cell would be provided with at least three constructs: a first construct containing the reporter gene operably linked to a promoter capable of being activated by a known transcriptional activator protein; a second construct that contains the gene of the known transcriptional activator protein under its native promoter; and a third construct that is the representative of the cDNA bank that is being screened for the identification of a protein that will activate transcription of the known transcriptional activator. In the presence of the protein encoded by the cDNA bank construct, the new transcriptional activator will effectively activate transcription of the known transcriptional activator, which, in turn, activates transcription of the reporter gene. This can be achieved also by operably linking the promoter of the activator gene directly to the reporter gene.

The method is also useful to identify not just regulatory proteins that regulate the transcription of other regulatory proteins, but also, to identify those transcriptional regulatory proteins that interact in an ancillary manner with another protein required for transcription so as to alter its ability to enhance or repress transcription, but that may not bind the promoter.

This method is not limited by the type of host and would be useful to identify any transcriptional regulatory protein for any host and in any host as long as the basic transcription machinery of such host would be expected to bind to the promoter operably linked to the reporter gene and to the transcriptional regulatory protein, as provided by the cDNA bank. For example, activator proteins in bacterial hosts could be identified by using a promoter capable of functioning in such host in the presence of the activator.

Using the method described above transcriptional activator proteins that regulate transcription in filamentous fungi can be identified. The identified proteins were called ACEI and ACEII and are capable of activating the promoter of the cellulase gene cbh1 that encodes the major cellulase cellobiohydrolase I (CBHI) protein.

ace1 and ace2 genes were obtained by screening of a T. reesei gene bank that had been induced to maximally express a variety of T. reesei extracellular enzymes including cellulases as well as xylanases and other hemicellulases. The encoded proteins contain DNA binding regions but show no other obvious amino acid similarity to any other protein known, not even when compared against the data base containing the complete yeast genome.

The ace1 cDNA sequence is deposited in plasmid pAS28 and the corresponding gene in plasmid pAS34 at the DSMZ (Deutsche Sammlung von Mikroorganismen und Zellkulturen GmbH) and assigned accession numbers DMS 11453 and 11451, respectively. The ace2 cDNA sequence is deposited in plasmid pAS26 and the corresponding gene in plasmid pAS33 at the DSMZ (Deutsche Sammlung von Mikroorganismen und Zellkulturen GmbH) and assigned accession numbers DMS 11454 and 11452, respectively.

It is possible to modulate the expression of ACEI and ACEII, and overexpress them under any inducible or constitutive promoter in Trichoderma or Aspergillus singly or together in various repressing, neutral or induced conditions in respect to cellulase production such as on glucose containing media or on media containing sorbitol, on cellulose or its derivatives cellobiose or sophorose, on xylan, lactose, or whey. Transforming a fungal host with clones capable of expressing ACEI and/or ACEII either under their own promoters or under the control of a desired heterologous promoter, enhances the levels of these proteins in the host cell and allows the maximal transcriptional expression of fungal proteins that are the natural targets for these proteins. Especially, such modulation is used to improve or modify expression of hydrolytic enzyme genes under their own, modified or heterologous promoters.

Additionally, the gene encoding any desired protein can be placed under the control of a promoter that is known to respond to the ACEI or ACEII protein, for example, the T. reesei cbh1 promoter, and expression of such protein can thereby be regulated or enhanced in a desired host cell. If such host cell naturally produced ACEI and/or ACEII then it may not be necessary to transform such a host with additional copies of the genes encoding these proteins.

However, if the host cell does not naturally produce ACEI or ACEII, or if the host cell produces relatively low levels of these proteins in a manner that may be limiting to the transcriptional induction capacity, then the host cell may be transformed with additional copies of the genes encoding one or both ACEI and ACEII as necessary and as provided according to the invention. If production is desired in conditions were the activators are not naturally produced, they can be overexpressed under a promoter functional in all conditions, e.g. the fungal glycerol phosphate dehydrogenase A (gpdA) promoter or cDNA1 promoter of *T. reesei*. The protein which expression is enhanced by producing the activators can be any homologous protein of Trichoderma or Aspergillus, or it can be any heterologous protein like the β-lactamase encoded by the lacZ gene of *E. coli* shown here.

Another way to enhance production of proteins is to modify the promoters in such a way that they contain additional copies of the ACEI and/or ACEII binding sites. Also promoters not normally under the regulation of the activators can be modified to contain one or more binding sites. By combining these methods the fungus can be manipulated to produce enzyme mixtures specifically tailored for each application.

The promoters and elements described herein are useful for expression of a desired coding or antisense RNA sequence in a fungal host. The process for genetically engineering such coding or antisense sequences, for expression under a promoter of the invention, is facilitated through the isolation and partial sequencing of pure protein encoding an enzyme of interest or by the cloning of genetic sequences which are capable of encoding such protein with polymerase chain reaction technologies; and through the expression of such genetic sequences. As used herein, the term "genetic sequences" is intended to refer to a nucleic acid molecule (preferably DNA). Genetic sequences that are capable of encoding a protein are derived from a variety of sources. These sources include genomic DNA, cDNA, synthetic DNA, and combinations thereof. The preferred source of genomic DNA is a fungal genomic bank. The preferred source of the cDNA is a cDNA bank prepared from fungal mRNA grown in conditions known to induce expression of the desired gene to produce mRNA or protein. However, since the genetic code is universal, a coding sequence from any host, including prokaryotic (bacterial) hosts, and any eukaryotic host plants, mammals, insects, yeast, and any cultured cell populations would be expected to function (encode the desired protein).

Genomic DNA may or may not include naturally occurring introns. Moreover, such genomic DNA may be obtained in association with the 5' promoter region of the gene sequences and/or with the 3' transcriptional termination region. According to the invention however, the native promoter region would be replaced with a promoter of the invention.

Such genomic DNA may also be obtained in association with the genetic sequences which encode the 5' non-translated region of the mRNA and/or with the genetic sequences which encode the 3' non-translated region. To the extent that a host cell can recognize the transcriptional and/or translational regulatory signals associated with the expression of the mRNA and protein, then the 5' and/or 3' non-transcribed regions of the native gene, and/or, the 5' and/or 3' non-translated regions of the mRNA may be retained and employed for transcriptional and translational regulation.

Genomic DNA can be extracted and purified from any host cell, especially a fungal host cell, which naturally expresses the desired protein by means well known in the art. A genomic DNA sequence may be shortened by means known in the art to isolate a desired gene from a chromosomal region that otherwise would contain more information than necessary for the utilization of this gene in the hosts of the invention. For example, restriction digestion may be utilized to cleave the full-length sequence at a desired location. Alternatively, or in addition, nucleases that cleave from the 3'-end of a DNA molecule may be used to digest a certain sequence to a shortened form, the desired length then being identified and purified by gel electrophoresis and DNA sequencing. Such nucleases include, for example, Exonuclease III and Bal31. Other nucleases are well known in the art.

For cloning into a vector, such suitable DNA preparations (either genomic DNA or cDNA) are randomly sheared or enzymatically cleaved, respectively, and ligated into appropriate vectors to form a recombinant gene (either genomic or cDNA) bank.

A DNA sequence encoding a desired protein or its functional derivatives may be inserted into a DNA vector in accordance with conventional techniques, including blunt-ending or staggered-ending teimini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis, T., (Maniatis, T. et al., *Molecular Cloning (A Laboratory Manual)*, Cold Spring Harbor Laboratory, second edition, 1988) and are well known in the art.

Libraries containing sequences coding for the desired gene may be screened and the desired gene sequence identified by any means which specifically selects for a sequence coding for such gene or protein such as, for example, a) by hybridization with an appropriate nucleic acid probe(s) containing a sequence specific for the DNA of this protein, or b) by hybridization-selected translational analysis in which native mRNA which hybridizes to the clone in question is translated in vitro and the translation products are further characterized, or, c) if the cloned genetic sequences are themselves capable of expressing mRNA, by immunoprecipitation of a translated protein product produced by the host containing the clone.

Oligonucleotide probes specific for a certain protein which can be used to identify clones to this protein can be designed from the knowledge of the amino acid sequence of the protein or from the knowledge of the nucleic acid sequence of the DNA encoding such protein or a related protein. Alternatively, antibodies may be raised against purified forms of the protein and used to identify the presence of unique protein determinants in transformants that express the desired cloned protein. When an amino acid sequence is listed horizontally, unless otherwise stated, the amino terminus is intended to be on the left end and the carboxy terminus is intended to be at the right end. Similarly, unless otherwise stated or apparent from the context, a nucleic acid sequence is presented with the 5' end on the left.

Because the genetic code is degenerate, more than one codon may be used to encode a particular amino acid. Peptide fragments can be analyzed to identify sequences of amino acids that may be encoded by oligonucleotides having the lowest degree of degeneracy. This is preferably accomplished by identifying sequences that contain amino acids which are encoded by only a single codon.

Although occasionally an amino acid sequence may be encoded by only a single oligonucleotide sequence, frequently the amino acid sequence may be encoded by any of a set of similar oligonucleotides. Importantly, whereas all of the members of this set contain oligonucleotide sequences which are capable of encoding the same peptide fragment and, thus, potentially contain the same oligonucleotide sequence as the gene which encodes the peptide fragment, only one member of the set contains the nucleotide sequence that is identical to the exon coding sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

Using the genetic code, one or more different oligonucleotides can be identified from the amino acid sequence, each of which would be capable of encoding the desired protein. The probability that a particular oligonucleotide will, in fact, constitute the actual protein encoding sequence can be estimated by considering abnormal base pairing relationships and the frequency with which a particular codon is actually used (to encode a particular amino acid) in eukaryotic cells. Using "codon usage rules," a single oligonucleotide sequence, or a set of oligonucleotide sequences, that contain a theoretical "most probable" nucleotide sequence capable of encoding the protein sequences is identified.

The suitable oligonucleotide, or set of oligonucleotides, which is capable of encoding a fragment of a certain gene (or which is complementary to such an oligonucleotide, or set of oligonucleotides) may be synthesized by means well known in the art (see, for example, *Oligonucleotides and Analogues, A Practical Approach,* F. Eckstein, ed., 1992, IRL Press, New York) and employed as a probe to identify and isolate a clone to such gene by techniques known in the art. Techniques of nucleic acid hybridization and clone identification are disclosed by Maniatis, T., et al., in: *Molecular Cloning, A Laboratory Manual,* Cold Spring Harbor Laboratories, Cold Spring Harbor, N.Y. (1982)), and by Hames, B. D., et al., in: *Nucleic Acid Hybridization, A Practical Approach,* IRL Press, Washington, D.C. (1985)). Those members of the above-described gene bank which are found to be capable of such hybridization are then analyzed to determine the extent and nature of coding sequences which they contain.

To facilitate the detection of a desired DNA coding sequence, the above-described DNA probe is labeled with a detectable group. Such detectable group can be any material having a detectable physical or chemical property. Such materials have been well-developed in the field of nucleic acid hybridization and in general most any label useful in such methods can be applied to the present invention. Particularly useful are radioactive labels, such as $^{32}P$, $^{3}H$, $^{14}C$, $^{35}S$, $^{125}I$, or the like. Any radioactive label may be employed which provides for an adequate signal and has a sufficient half-life. If single stranded, the oligonucleotide may be radioactively labeled using kinase reactions. Alternatively, polynucleotides are also useful as nucleic acid hybridization probes when labeled with a non-radioactive marker such as biotin, an enzyme or a fluorescent group.

Thus, in summary, the elucidation of a partial protein sequence, permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe(s) for the identification and isolation of clones containing a gene.

In an alternative way of cloning a gene, a bank is prepared using an expression vector, by cloning DNA or, more preferably cDNA prepared from a cell capable of expressing the protein into an expression vector. The bank is then screened for members which express the desired protein, for example, by screening the bank with antibodies to the protein.

The above discussed methods are, therefore, capable of identifying genetic sequences that are capable of encoding a protein or biologically active or antigenic fragments of this protein. The desired coding sequence may be further characterized by demonstrating its ability to encode a protein having the ability to bind antibody in a specific manner, the ability to elicit the production of antibody which are capable of binding to the native, non-recombinant protein, the ability to provide a enzymatic activity to a cell that is a property of the protein, and the ability to provide a non-enzymatic (but specific) function to a recipient cell, among others.

In order to produce the recombinant protein in the vectors of the invention, it is desirable to operably link such coding sequences to the glucose regulatable (either repressible or derepressed) promoters of the invention. When the coding sequence and the operably linked promoter of the invention are introduced into a recipient eukaryotic cell (preferably a fungal host cell) as a non-replicating DNA (or RNA), non-integrating molecule, the expression of the encoded protein may occur through the transient (nonstable) expression of the introduced sequence.

Preferably the coding, sequence is introduced on a DNA molecule, such as a closed circular or linear molecule that is incapable of autonomous replication, Preferably, when a filamentous fungi is the host, the DNA molecule is a linear molecule that integrates into the host chromosome. Genetically stable transformants may be constructed with vector systems, or transformation systems, whereby a desired DNA is integrated into the host chromosome. Such integration may occur de novo within the cell or, be assisted by transformation with a vector which functionally inserts itself into the host chromosome.

The gene encoding the desired protein operably linked to the promoter of the invention may be placed with a transformation marker gene in one plasmid construction and introduced into the host cells by transformation, or, the marker gene may be on a separate construct for co-transformation with the coding sequence construct into the host cell. The nature of the vector will depend on the host organism. In the practical realization of the invention the filamentous fungus Trichoderma has been employed as a model. Thus, for Trichoderma and especially for *T. reesei,* vectors incorporating DNA that provides for integration of the expression cassette (the coding sequence operably linked to its transcriptional and translational regulatory elements) into the host's chromosome are preferred. It is not necessary to target the chromosomal insertion to a specific site. However, targeting the integration to a specific locus may be achieved by providing specific coding or flanking sequences on the recombinant construct, in an amount sufficient to direct integration to this locus at a relevant frequency.

Cells that have stably integrated the introduced DNA into their chromosomes are selected by also introducing one or more markers which allow for selection of host cells which contain the expression vector in the chromosome, for example the marker may provide biocide resistance, e.g., resistance to antibiotics, or heavy metals, such as copper, or the like. The selectable marker gene can either be directly linked to the DNA gene sequences to be expressed, or introduced into the same cell by co-transformation. A genetic marker especially for the transformation of the hosts of the invention is amdS, encoding acetamidase and thus enabling Trichoderina to grow on acetamide as the only nitrogen source. Selectable markers for use in transforming filamentous fungi include, for example, acetamidase (the amdS gene), benomyl resistance, oligomycin resistance, hygromycin resistance, aminoglycoside resistance, bleomycin resistance; and, with auxotrophic mutants, ornithine carbamoyltransferase (OCTase or the argB gene). The use of such markers is also reviewed in Finkelstein, D. B. in: *Biotechnology of Filamentous Fungi: Technology and Products*, Chapter 6, Finkelstein, D. B. et al., eds., Butterworth-Heiremann, publishers, Stoneham, Mass., (1992), pp. 113–156).

To express a desired protein and/or its active derivatives, transcriptional and translational signals recognizable by an appropriate host are necessary. The cloned coding sequences, obtained through the methods described above, and preferably in a double-stranded form, may be operably linked to sequences controlling transcriptional expression in an expression vector, and introduced into a host cell, either prokaryote or eukaryote, to produce recombinant protein or a functional derivative thereof. Depending upon which strand of the coding sequence is operably linked to the sequences controlling transcriptional expression, it is also possible to express antisense RNA or a functional derivative thereof.

Expression of the protein in different hosts may result in different post-translational modifications which may alter the properties of the protein. Preferably, the present invention encompasses the expression of the protein or a functional derivative thereof in eukaryotic cells, and especially in fungus.

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide.

An operable linkage is a linkage in which a sequence is connected to a regulatory sequence (or sequences) in such a way as to place expression of the sequence under the influence or control of the regulatory sequence. A coding sequence and a promoter region sequence linked to the 5' end of the coding sequence are said to be operably linked if induction of promoter function results in the transcription of RNA encoding the desired protein (or antisense RNA) and if the nature of the linkage between the two DNA sequences does not (1) result in the introduction of a frame-shift mutation, (2) interfere with the ability of the expression regulatory sequences to direct the expression of the protein (or antisense RNA), or (3) interfere with the ability of the DNA template to be transcribed. Thus, a promoter region would be operably linked to a DNA sequence if the promoter was capable of effecting transcription of that DNA sequence.

The precise nature of the regulatory regions needed for gene expression may vary between species or cell types, but shall in general include, as necessary, 5' non-transcribing and 5' non-translating (non-coding) sequences involved with initiation of transcription and translation respectively, such as the TATA box, capping sequence, CAAT sequence, and the like, with those elements necessary for the promoter sequence being provided by the promoters of the invention. Such transcriptional control sequences may also include enhancer sequences or upstream activator sequences, as desired.

Expression of a protein in eukaryotic hosts such as fungus requires the use of regulatory regions functional in such hosts, and preferably fungal regulatory systems. A wide variety of transcriptional and translational regulatory sequences can be employed, depending upon the nature of the host. Preferably, these regulatory signals are associated in their native state with a particular gene which is capable of a high level of expression in the host cell.

In eukaryotes, where transcription is not linked to translation, such control regions may or may not provide an initiator methionine (AUG) codon, depending on whether the cloned sequence contains such a methionine. Such regions will, in general, include a promoter of the invention sufficient to direct the initiation of the synthesis of the desired RNA in the host cell.

As is widely known translation of eukaryotic mRNA is initiated at the codon which encodes the first methionine. For this reason, it is preferable to ensure that the linkage between a eukaryotic promoter and a DNA sequence which encodes the desired protein, or a functional derivative thereof, does not contain any intervening codons which are capable of encoding a methionine. The presence of such codons results either in a formation of a fusion protein (if the AUG codon is in the same reading frame as the protein-coding DNA sequence) or a frame-shift mutation (if the AUG codon is not in the same reading frame as the protein-coding sequence).

It may be desired to construct a fusion product that contains a partial coding sequence (usually at the amino terminal end) of a protein and a second coding sequence (partial or complete) of a second protein. The first coding sequence may or may not function as a signal sequence for secretion of the protein from the host cell. For example, the sequence coding for desired protein may be linked to a signal sequence which will allow secretion of the protein from, or the compartmentalization of the protein in, a particular host. Such fusion protein sequences may be designed with or without specific protease sites such that a desired peptide sequence is amenable to subsequent removal. In a preferred embodiment, the native signal sequence of a fungal protein is used, or a functional derivative of that sequence that retains the ability to direct the secretion of the peptide that is operably linked to it.

Secretion signals for the filamentous fungi will generally function outside of their native host. For example, secretion signals from one type of Trichoderma, such as *T. reesei*, will function in another type of Trichoderma and in other filamentous fungi. Aspergillus leader/secretion signal elements also function in Trichoderma.

If desired, the non-transcribed and/or non-translated regions 3' to the sequence coding for a desired protein can be obtained by the above-described cloning methods. The 3'-non-transcribed region may be retained for its transcriptional termination regulatory sequence elements, or for those elements which direct polyadenylation in eukaryotic cells. Where the native expression control sequences signals do not function satisfactorily in a host cell, then sequences functional in the host cell may be substituted.

The vectors of the invention may further comprise other operably linked regulatory elements such as DNA sequences to target insertion at a desired site in the chromosome. The vectors may also contain sequences that confer antibiotic resistance, or origins of replication for maintenance of the vector in one or more host cells, especially if the vector is designed to be capable of being maintained in a bacterial host. Thus, in another embodiment, especially for maintenance of the vectors of the invention in prokaryotic cells, or in yeast *S. cerevisiae* cells, the introduced sequence is incorporated into a plasmid or viral vector capable of autonomous replication in the recipient host. Any of a wide variety of vectors may be employed for this purpose. In Bacillus hosts, integration of the desired DNA may be necessary.

Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

When it is desired to use *S. cerevisiae* as a host for a shuttle vector, preferred *S. cerevisiae* yeast plasmids include those containing the 2-micron circle, etc., or their derivatives. Such plasmids are well known in the art (Botstein, D., et al., *Miami Wntr. Symp.* 19: 265–274 (1982); Broach, J. R., in: *The Molecular Biology of the Yeast Saccharomyces: Life Cycle and Inheritance*, Cold Spring Harbor Laboratory, Cold Spring Harbor, N.Y., p. 445–470 (1981); Broach, J. R., *Cell* 28: 203–204 (1982); Bollon, D. P., et al., *J. Clin. Hematol. Oncol.* 10: 39–48 (1980); Maniatis, T., In: *Cell Biology: A Comprehensive Treatise*, Vol.3, Gene Expression, Academic Press, NY, pp. 563–608 (1980)), and are commercially available.

Once the vector or DNA sequence containing the construct(s) is prepared for expression, the DNA construct (s) is introduced into an appropriate host cell by any of a variety of suitable means, including transformation. After the introduction of the vector, recipient cells are grown in a selective medium, which selects for the growth of vector-containing cells. If the gene of interest is being expressed under the control of one of the glucose derepressed promoters of the invention, and if this medium includes glucose, expression of the cloned gene sequence(s) results in the production of the desired protein that is operably linked to the glucose derepressed promoter of the invention. This expression can take place in a continuous manner in the transformed cells (for example, if the promoter expresses in the absence of an inducer like sophorose), or in a controlled manner, for example, by induction of expression by inclusion of inducing amounts of sophorose in the medium. Useful sophorose concentrations range from about 0.1 mM to about 20 mM. Useful glucose concentrations range from about 0.5% to 5%.

Fungal transformation is carried out also accordingly to techniques known in the art, for example, using, for example, homologous recombination to stably insert a gene into the fungal host and/or to destroy the ability of the host cell to express a certain protein.

Fungi useful as recombinant hosts for the purpose of the invention include, e.g. Trichoderma, Aspergillus, *Claviceps purpurea*, *Penicillium chrysogenum*, *Magnaporthe grisea*, Neurospora, Mycosphaerella spp., *Collectotrichum trifolii*, the dimorphic fungus *Histoplasmia capsulatum*, *Nectia haematococca* (anamorph: *Fusarium solani* f. sp. *phaseoli* and f. sp. *pisi*), *Ustilago violacea*, *Ustilago maydis*, *Cephalosporium acremonium*, *Schizophyllum commune*, *Podospora anserina*, *Sordaria macrospora*, *Mucor circinelloides*, and *Collectotrichum capsici*. Transformation and selection techniques for each of these fungi have been described (reviewed in Finkelstein, D. B. in: *Biotechnology of Filamentous Fungi: Technology and Products*, Chapter 6, Finkelstein, D. B. et al., eds., Butterworth-Heinemann, publishers, Stoneham, Mass., (1992), pp. 113–156). Especially preferred are *Trichoderma reesei*, *T. harzianum*, *T. longibrachiatum*, *T. viride*, *T. koningii*, *Aspergillus nidulans*, *A. niger*, *A. terreus*, *A. ficum*, *A. oryzae*, *A. awamori* and *Neurospora crassa*.

The hosts of the invention are meant to include any member of the Trichoderma genus. Trichoderma are classified on the basis of morphological evidence of similarity. *T. reesei* was formerly known as *T. viride* Pers. or *T. koningii* Oudem; sometimes it was classified as a distinct species of the *T. longibrachiatum* group. The entire genus Trichoderma, in general, is characterized by rapidly growing colonies bearing tufted or pustulate, repeatedly branched conidiophores with lageniform phialides and hyaline or green conidia borne in slimy heads (Bissett, J., *Can. J. Bot.* 62: 924–931 (1984)).

The fungus called *T. reesei* is clearly defined as a genetic family originating from the strain QM6a, that is, a family of strains possessing a common genetic background originating from a single nucleus of the particular isolate QM6a. Only those strains are called *T. reesei*.

Classification by morphological means is problematic because of the close similarity discussed above and the first recently published molecular data from DNA-fingerprint analysis and the hybridization pattern of the cellobiohydrolase 2 (cbh2) gene in *T. reesei* and *T. longibrachiatum* clearly indicate a differentiation of these strains (Meyer, W. et al., *Curr. Genet.* 21: 27–30 (1992); Morawetz, R. et al., *Curr. Genet.* 21: 31–36 (1992)).

However, there is evidence of similarity between different Trichoderma species at the molecular level that is found in the conservation of nucleic acid and amino acid sequences of macromolecular entities shared by the various Trichoderma species. For example, Cheng, C., et al., *Nucl. Acids. Res.* 18: 5559 (1990), discloses the nucleotide sequence of *T. viride* cbh1. The gene was isolated using a probe based on the *T. reesei* sequence. The authors note that there is a 95% homology between the amino acid sequences of the *T. viride* and *T. reesei* gene. Goldman, G. H. et al., *Nuci. Acids Res.* 18: 6717 (1990), discloses the nucleotide sequence of phosphoglycerate kinases from *T. viride* and notes that the deduced amino acid sequence is 81% homologous with the phosphoglycerate kinase gene from *T. reesei*. Thus, the species classified to *T. viride* and *T. reesei* are genetically very close to each other.

In addition, there is a high similarity of transformation conditions among the Trichoderma. Although practically all the industrially important species of Trichoderma can be found in the formerly discussed Trichoderma section Longbrachiatum, there are some other species of Trichoderma that are not assigned to this section. Such a species is, for example, *Trichoderma harzianum*, which acts as a biocontrol agent against plant pathogens. A transformation system has also been developed for this Trichoderma species (Herrera-Estrella, A. et al., *Molec. Microbiol.* 4: 839–843 (1990)) that is essentially the same as that taught for *T. reesei* (EP 244,234). Thus, even though *Trichoderma harzianum* is not assigned to the section Longibrachiatum, the method used by Herrera-Estrella in the preparation of spheroplasts before transformation is the same. The teachings of Herrera-Estrella show that there is not a significant diversity of Trichoderma spp. such that the transformation system of the invention would not be expected to function in all Trichoderma. *T. reesei* is available from a variety of sources, such as, for example, ATCC26921 (*T. reesei* strain QM9414).

Further, there is a common functionality of fungal transcriptional control signals among fungal species. At least three *A. nidulans* promoter sequences, amdS, argB, and gpd, have been shown to function in *T. reesei*. For amdS and argB, only one or two copies of the gene are sufficient to being about a selectable phenotypes. Fungal genes can often by successfully expressed across different species. Therefore, it is to be expected that the promoters of the invention would be useful in all Trichoderma and in filamentous fungi other than Trichoderma.

Many species of fungi, and especially Trichoderma, are available from a wide variety of resource centers that contain fungal culture collections. In addition, Trichoderma species are catalogued in various databases. These resources and databases are summarized by O'Donnell, K. et al., in *Biochemistry of Filamentous Fungi. Technology and Products*, D. B. Fingelstein et al., eds., Butterworth-Heinemann, Sloneham, Mass., USA, 1992, pp. 3–39.

After the introduction of the vector and selection of the transformant, recipient cells are grown in a selective medium, which selects for the growth of vector-containing cells. Expression of the cloned gene sequence(s) under control of the promoter of the invention results in the synthesis and secretion of the desired heterologous or homologous protein, or in the production of a fragment of this protein, into the medium of the host cell.

Any desired coding sequence may be expressed under the control of the promoters of the invention. In a preferred embodiment, the coding sequence is the sequence of an enzyme that is capable of hydrolysing lignocellulose. Examples of such sequences include a DNA sequence encoding cellobiohydrolase I (CBHI), cellobiohydrolase II (CBHII), endoglucanase I (EGI), endoglucanase II (EGII), endoglucanase III (EGIII), β-glucosidases, xylanases (including endoxylanases and β-xylosidase), side-group cleaving activities, (for example, α-arabinosidase, α-D-glucuronidase, and acetyl esicrase), mannanases, pectinases (for example, endopolygalacturonase, exo-polygalacturonase, pectinesterase, or, pectin and pectin acid lyase), and enzymes of lignin polymer degradation, (for example, lignin peroxidase LIII from *Phlebia radiata* (Saloheimo et al., *Gene* 85: 343–351 (1989)), or the gene for another ligninase, laccase or Mn peroxidase (Kirk, In: *Biochemistry and Genetics of Cellulose Degradation*, Aubert et al. (eds.), FEMS Symposium No. 43, Academic Press, Harcourt, Brace Jovanovitch Publishers, London. pp. 315–332 (1988))). The cloning of the cellulolytic enzyme genes has been described and recently reviewed (Teeri, T. T. in: *Biotechnology of Filamentous Fungi: Technology and Products*, Chapter 14, Finkelstein, D. B. et al., eds., Butterworth-Heinemann, publishers Stoneham, Mass., (1992), pp. 417–445). The gene for the native cellobiohydrolase CBHI sequence has been cloned by Shoemaker et al. (Shoemaker, S., et al., *Bio/Technology* 1: 691–696 (1983)) and Teeri et al. (Teeri, T., et al., *Bio/Technology* 1: 696–699 (1983)) and the entire nucleotide sequence of the gene is known (Shoemaker, S., et al., *Bio/Technology* 1: 691–696 (1983)). From *T. reesei*, the gene for the major endoglucanase (EGI) has also been cloned and characterized (Penttilä, M., et al., *Gene* 45: 253–263 (1986); Patent Application EP 137,280; Van Arstel, J. N. V., et al., *Bio/Technology* 5: 60–64). Other isolated cellulase genes include cbh2 (Patent Application WO 85/04672; Chen, C. M., et al., *Bio/Technology* 5: 274–278 (1987)) and egl3 (Saloheimo, M., et al., *Gene* 63: 11–21 (1988)). The genes for the two endo-β-xylanases of *T. reesei* (xln1 and xln2) have been cloned and described in WO 93/24621. The xylanase proteins have been purified and characterized (Tenkanen, M. et al, *Proceeding of the Xylans and Xylanases Symposium*, Wageningen, Holland (1991)).

The expressed protein may be purified or isolated, as desired, from the medium of the host in accordance with conventional conditions, such as extraction, precipitation, chromatography, affinity chromatography, electrophoresis, or the like. For example, the cells may be collected by centrifugation, or with suitable buffers, lysed, and the protein isolated by column chromatography for example, on DEAE-cellulose, phosphocellulose, polyribocytidylic acid-agarose, hydroxyapatite or by electrophoresis or immuno-precipitation.

The protein that is expressed under direction of the promoters of the invention can also be useful in an enzyme preparation. By "enzyme preparation" is meant a composition containing enzymes. Preferably, the enzymes have been extracted from (either partially or completely purified from) a microbe or the medium used to grow such microbe. "Extracted from" means that the desired enzymes are separated from the cellular mass. This can be performed by any method that achieves this goal, including breaking cells and also simply removing the culture medium from spent cells. Therefore, the term "enzyme preparation" includes compositions containing medium previously used to culture a desired microbe(s) and any enzymes that have been released from the microbial cells into such medium during the culture or downstream processing steps.

The host used to express the desired protein may also be substantially incapable of synthesizing one or more enzymes or proteins native to that host. By a host that is "substantially incapable" of synthesizing one or more enzymes is meant a host in which the activity of one or more of the listed enzymes is repressed, deficient, or absent when compared to the wild-type.

The manner and method of carrying out the present invention may be more fully understood by those of skill by reference to the following examples, which examples are not intended in any manner to limit the scope of the present invention or of the claims directed thereto.

EXAMPLE 1

Materials and Methods
Fungal Strains and Shake Flask Cultivations

The *T. reesei* strain QM9414 (Mandels, M. et al., *Appl. Microbiol.* 21, 152–154 (1971); VTT-D-74075) was used throughout the study. It was grown on potato dextrose agar (Difco) to obtain spores which were suspended into 0.8% NaCl—0.025% Tween 80—20% glycerol and stored at −70° C.

Trichoderma minimal medium, pH 4.8, (Penttilä, M. et al, *Gene* 61:155–164 (1987)) was prepared with or without 0.2% proteose peptone and was supplemented with 2% sorbitol or 5% glucose. 50 ml of growth media in 250 ml conical shake flasks were inoculated with $10^7$ spores and Trichoderma was grown shaking at 200 rpm at 28° C. for 48 to 87 h depending on the growth. Into some sorbitol-based cultures α-sophorose (Serva) was added to 1 mM concentration twice, at 72 and 82 h, to ensure prolonged high level of induction of cellulase genes. Mycelia were always collected 15 h after the first addition of sophorose which is representative of cellulase mRNA peak levels. Northern analyses also included mycelia grown for the same time without sophorose addition as well as mycelia grown for 15 h shorter time period. Since the latter two cultivations always gave the same result, only results from the longer cultivation without sophorose addition are shown. The amount of glucose in the medium was measured daily using the GOD-Perid system (Boehringer Mannheim). Mycelia were harvested by filtration through GF/B glass microfibre filters (Whatman), washed with sterile water or 0.7% NaCl and stored at −70° C.

Plasmid Constructions

E. coli DH5α was used as a host for transformations and maintenance of the plasmids. All ligation joints and PCR amplified DNA fragments were sequenced from double stranded vectors using the dideoxy termination method, sequence specific primers, and the Sequenase™ version 2 DNA polymerase (USB). The Vent™ polymerase (NEB) was used for PCR amplification.

Figure 2:
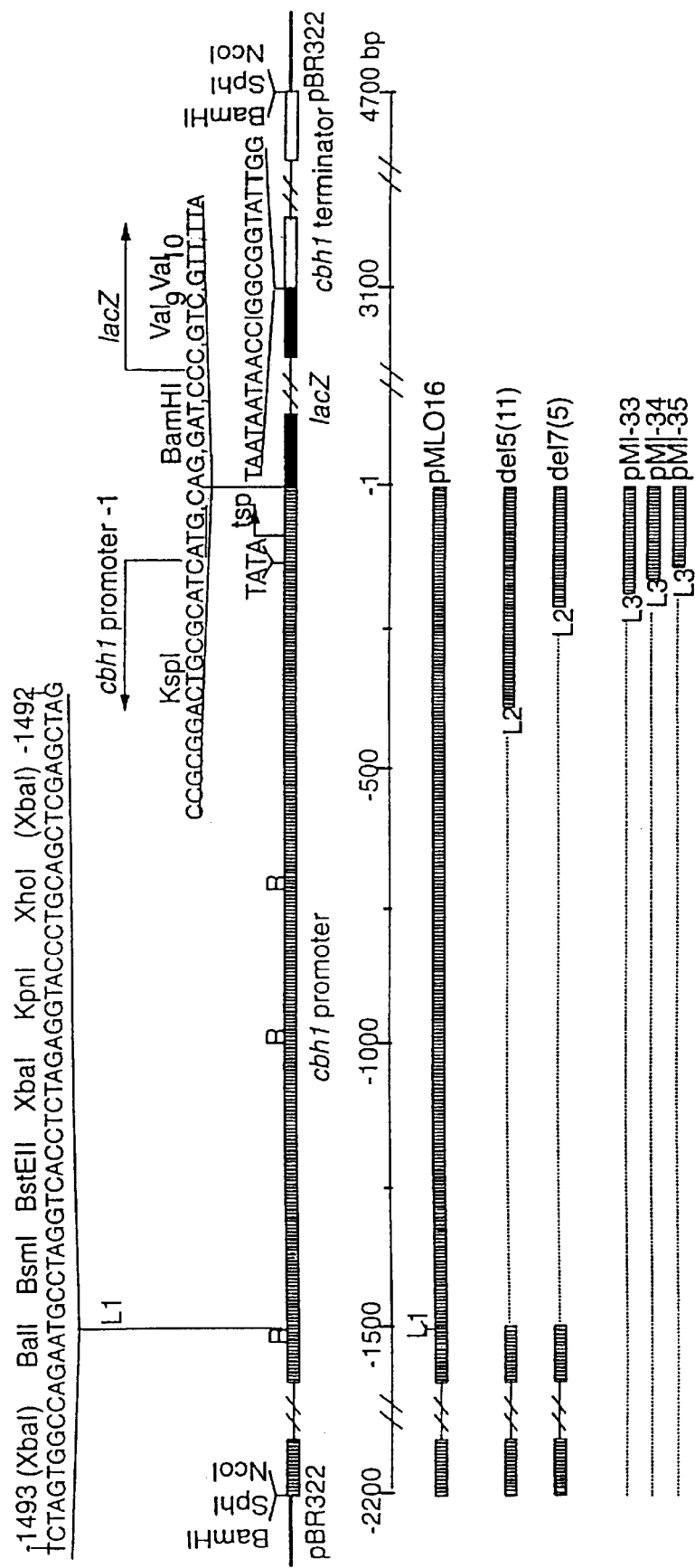
FIG. 2. Schematic representation of the β-galactosidase expression vector pMLO16 and the derivatives containing mutant cbh1 promoters. pMLO16 consists of the *T. reesei* wild type cbh1 promoter (hashed boxes), *E. coli* lacZ (black boxes labeled "lacZ" in the coding sequence) and the *T. reesei* cbh1 terminator (open boxes) in the vector pBR322 (- - -). The putative TATA-box is situated at −132 and the major transcription start points (tsp) at −83 and −93 upstream of the initiator ATG. Nucleotide sequences are shown for the region in which the −1 nucleotide of The cbh1 promoter, the initiator ATG, and the lacZ gene are joined (SEQ ID No.22) and for the region in which the 5' end of the lacZ gene and the 3' end of the cbh1 terminator (SEQ ID No.23) are joined. Different variants of the polylinker L1 were generated between the nucleotides −1497 and −1498 (numbering according to the wild type promoter) in construction of the different vectors. The linkers (L1–L3) contain the following restriction enzyme cleavage sites, L1 (SEQ ID No.21): BalI, BsmIU, BstEII, XbaI, KpnI, PstI, XhoI; L2: BalI, BsmI, BstEII, XbaI; L3: BalI, BsmI BstEII. Other relevant restriction enzyme cleavage sites are also shown. See Example 1 and Table 1 for details of the vector constructions.

The expression construct pMLO16 (FIG.2) consists of the wild type T.reesei cbh1 promoter (Nakari, T. et al., WO 94/04673) beginning at an EcoRI site located 2.2 kb upstream of the protein coding region (Teeri. T. et al., Bio/Technology 1: 696–699 (1983)), a 3.1 kb E. coli lacZ fragment of the plasmid pAN924–21 (van Gorcom, R.F.M. et al., Gene 40: 99–106 (1985)), and a cbh1 terminator as a 1.6 kb AvaII-BamHI fragment (Shoemaker, S. et al., Bio/Technology 1: 691–695 (1983), Teeri, T. et al., Bio/Technology 1: 696–699 (1983)), all cloned into the 2.3 kb EcoRI-PvuII fragment of pBR322. The exact joint between the −1 nucleotide of the cbh1 promoter, the initiator ATG and the lacZ gene was constructed using an oligonucleotide (FIG. 2). A polylinker containing multiple restriction sites (FIG. 2) was inserted into the single XbaI site in the cbh1 promoter 1498 bp upstream of the translation initiation codon. A linker containing a SalI restriction site was cloned into the EcoRI site at the 5' end of the cbh1 promoter and a linker containing a SphI site at the 3' end of the cbh1 terminator (FIG. 2). Other lacZ expression vectors described below contain modified cbh1 promoters and are derivatives of pMLO16 (FIG. 2). Sequences of oligonucleotides used as PCR primers in construction of mutant cbh1 promoters are listed in Table 1.

Additional shorter forms of the promoter, pMI-33, pMI-34 and pMI-35, of 184, 161 and 140 bp in length, respectively (FIG. 2), were constructed using PCR. To construct pMI-33 primers 2 and 1 (SEQ ID Nos. 4 and 3, Table 1) were used. The amplified fragment was cut with BstEII-KspI and ligated with BstEII-KspI cut pMLO16. pMI-34 and pMI-35 were constructed in the same way using primer pairs 3 and 1 (SEQ ID Nos. 5 and 3, Table 1), and 4 and 1 (SEQ ID Nos. 6 and 3, Table 1), respectively.

Transformation of Trichoderma

Trichodermareesei strain QM9414 was transformed according to Penttilä, M. et al., Gene 61: 155–164 (1987)). Prior to transformations expression cassettes consisting of the cbh1 promoter, lacZ, and cbh1 terminator were released from the vector sequences with SalI and SphI cutting at the 5' end of the promoter and at the 3' end of the terminator, respectively, if not otherwise stated in the text. This DNA (20 µg) was purified by phenol extraction and cotransformed with 3 µg of the plasmid p3SR2 (Hynes, M.J. et al, Mol. Cell. Biol. 3: 1430–1439 (1983)) that contains the Aspergillus nidulans amdS gene as a selection marker enabling growth of the transformants on acetamide as the sole nitrogen source. Transformants were streaked twice on selective medium, then transferred to potato dextrose agar (Difco) for sporulation. Spore suspensions were plated out on selective medium to obtain colonies derived from single spores for further analyses.

β-Galactosidase Plate Assays

Solid Trichoderma minimal medium (Penttilä, M. et al., Gene 61: 155–164 (1987)), pH adjusted to 7 with KOH, supplemented with 0.2% peptone, and with either 2% glucose-2% fructose, 2% cellobiose or 2% sorbitol as carbon sources, was pipetted into the wells of sterile 96-well microtiter plates. The wells were inoculated with approximately $10^5$ spores and the fungi were grown for at least 24

TABLE 1

Sequences of the PCR primers used for plasmid construction.

| No. | Sequence | SEQ ID No. |
|---|---|---|
| 1 |         -1        KspI<br>5'gggaatttcatGATGCGCAGT<u>CCGCGG</u> (L)<sup>a</sup> | 3 |
| 2 |     BstEII    -184<br>5'gggaattc<u>ggtcacc</u>AAAGATAGCCTCATTAAACGG (U)<sup>a</sup> | 4 |
| 3 |     BstEII    -161<br>5'gggaattc<u>ggtcacc</u>TGAGCTAGTAGGCAAAGTCAGC (U)<sup>a</sup> | 5 |
| 4 |     BstEII    -140<br>5'gggaattc<u>ggtcac</u>CGAATGTGTATATATAAAGGTTCG (U)<sup>a</sup> | 6 |

[a](U) refers to upper strand and (L) to the lower strand of the promoter, according to which the primer has been designed. Capital letters denote the nucleotides corresponding to the wild type cbh1 promoter sequences. The designed alterations and nucleotides included for cloning purposes are in lower case. Restriction sites used to clone the PCR fragments into the expression vectors are underlined. Position of the most 5' nucleotide corresponding to cbh1 promoter sequences relative to the initiator ATG is indicated.

A series of progressive unidirectional deletions was made to the cbh1 promoter in pMLO16 cut with KpnI-XhoI using the Erase-a-base system (Promega). Deletions started from the polylinker at −1497 and proceeded towards the protein coding region resulting in plasmids del5(11), and del7(5) (see FIG. 2 and Ilmen et al., Mol Gen Genet: 253: 303–314 (1996).

h at 28° C. In certain experiments 10 µl sophorose (20 mg/ml) was added on top of the colonies 3 h before the βGal assay. βGal activity was assayed by adding 10 µl of 5-bromo-4-chloro-3-indolyl-β-D-galactopyranoside (X-gal, 10 mg/ml) on top of the colonies, incubating the plates at room temperature and following the formation of blue color is an indication of βGal activity. The plates were photographed 3–5 h after addition of X-gal.

Identification of CBHI-Negative Transformants

Fungal clones were grown without shaking at 28° C. for 3 days in microtiter plate wells containing 200 ml liquid Trichoderma MM (Penttila, M. et al., Gene 61: 155–164 (1987)) supplemented with 0.2% peptone and 2% lactose, a cellulase-inducing carbon source. 40 μl of growth medium was dot blotted onto nitrocellulose membranes and CBHI was detected using the CBHI specific monoclonal antibodies CI-261 or CI-271 (Aho, S. et al., Eur. J. Biochem. 200: 643–649 (1991)) (kindly provided by Dr. Rolf Bühler, Alko Research Laboratory, Helsinki, Finland). Anti-CBHI antibodies were detected using alkaline-phosphatase conjugated anti-mouse polyvalent antibodies (Sigma), and the complex was further detected using the ProtoBlot reagents (Promega).

Southern Analyses

Fungal DNA was isolated using the method of Raeder, U. et al. Lett. Appl. Microbiol. 1: 17–20 (1985). For Southern analyses DNA was digested with BamHI-BstEII in order to check correct integration of the transformed expression constructs into the cbh1 locus at the promoter side. ClaI-XhoI or ClaI-XhoI-XbaI digestions were used to check integration at the terminator side, and to reveal possible integration of multiple copies in the cbh1 locus. XbaI digestion was used to reveal the presence of the site specific mutation generated in the cbh1 promoter. DNA fragments (2 μg) were size fractionated in 0.8% agarose gels and blotted onto nylon membranes using standard methods. Blots were hybridized with probes specific for the cbh1 promoter, lacZ and cbh1 cDNA. Hybridization was done in 50% formamide—5×Denhardt's—5×SSPE—0.1% SDS—100 μg/ml denatured herring sperm DNA—1 μg/ml polyA DNA at 42° C. overnight and washed twice for 5 min in 2×SSC at room temperature, and for 30 min in 2×SSC—0.1% SDS at 65° C.

Northern Analysis

Total fungal RNA was prepared according to Chirgwin, J.M. et al, Biochemistry 18: 5294–5299(1979). In all experiments mycelia were washed with 0.7% NaCl after harvesting in order to minimize RNA degradation. For Northern analyses 2–5 μg RNA was glyoxylated and separated in gel according to Maniatis, T. et al., Molecular cloning: A laboratory manual. Cold Spring Harbor Laboratory, Cold Spring Harbor. N.Y. (1982) and stained with acridine orange prior to blotting. RNA was blotted in 20×SSC in capillary flow onto Hybond N nylon membranes. Northern hybridizations were done at 42° C. in 50% formamide—10% dextran sulphate—1% SDS—1M NaCl—125 μg/ml denatured herring sperm DNA overnight and washed at 42° C. in 5×SSPE, twice in 1×SSPE—0.1% SDS and twice in 0.1% SSPE—0.1% SDS, for 15 min each wash.

Probes for Nucleic Acid Hybridizations

Probes were the complete T. reesei cbh1, cbh2 (Penttilä, M.E. et al, Gene 63: 103–112 (1988)) and egl1 cDNAs (Penttilä. M.E. et al., Yeast 3: 175–185 (1987)), the 2.2 kb EcoRI- BamHI fragment of the chh1 promoter obtained from pMLO16, and the 3.1 kb long E. coli lacZ gene from pMLO16. The T. reesei acting probe covering the fifth exon of the gene was amplified from chromosomal DNA using sequence specific primers (Matheucci, E. et al, Gene 161: 103–106 (1995)). Probes were labeled using the Random Primed DNA Labeling Kit (Boehringer Mannheim) and [α-$^{32}$P]dCTP (Amersham).

EXAMPLE 2

Promoter Assay

For functional analysis of the cbh1 promoter the E. coli β-galactosidase gene lacZ was used as a reporter. The basic expression vector constructed, pMLO16, consists of 2.2 kb of the wild type cbh1 promoter linked to the 3.1 kb protein encoding region of lacZ, followed by a 1.6 kb cbh1 terminator (FIG. 2). A polylinker was inserted into the cbh1 promoter region of both plasmids at the XbaI site at 1497 bp upstream of the protein coding region to enable generation of mutant promoters. The expression cassettes (see later) were co-transformed into the T.reesei strain QM9414 together with the selection marker for transformation.

β-galactosidase (βGal) producing colonies (βGal$^+$) could be screened among the transformants based on their blue color on Petri dishes containing the chromogenic substrate X-gal. However, to rapidly screen dozens of transformants, to obtain reliable and repeatable results, and to reduce the cost of the experiments, a convenient microtiter plate assay was developed. Microtiter plate wells containing solid minimal medium were inoculated with suspensions containing equal amount of spores of the tested strains. The pH of the medium was adjusted to 7 that was found optimal for detection of E. Coli βGal without interference by the endogenous βGal activity of T. reesei, which has a lower pH optimum. The fungi were grown for 1 or 2 days, where after X-gal was added on top of the colonies and the formation of blue color as an indication of βGal activity was followed over several hours. Initial screening for βGal-producing transformants was done on cellobiose containing medium that allows for lacZ expression from the cbh1 promoter. On the average, 70–80% of the transformants were βGal$^+$. The plate assay circumvents the use of more laborious analyses of βGal activities of cellular extracts as an initial selection screen of the transformants to be studied in detail.

lacZ was expressed from the wild type cbh1 promoter in the same carbon source-dependent fashion as endogenous chh1. Strong induction of βGal expression was achieved by growing the fungi on sorbitol followed by sophorose addition. Colonies incubated with sophorose turned blue whereas those grown on sorbitol without sophorose addition remained pale. In repressing conditions transformants with lacZ joined to the wild type promoter remained pale as expected (see later). 2% glucose—2% fructose containing medium was generally used in the plate assay to monitor expression under repressing conditions, because lacZ expression was more efficiently repressed on this medium than if only glucose was used as the carbon source.

In the absence of stable autonomously replicating plasmids in filamentous fungi, the expression constructs need to be targeted to a specific locus in the genome to avoid copy number and position effects in gene regulation studies. All the constructs were designed to be targeted into the cbh1 locus via homologous recombination through the promoter and terminator regions thus avoiding any extra vector sequences which might affect promoter function (our unpublished observations). To achieve this, the expression cassette was released prior to transformation from the vector sequences using restriction enzymes cutting 5' of the cbh1 promoter and 3' of the terminator (see FIG. 2 ). In order to find transformants in which the endogenous cbh1 locus had been replaced by lacZ, the βGal$^+$ colonies were screened for lack of CBHI protein production using anti-CBHI antibodies. Integration of the transformed construct into the cbh1 locus in a correct way and simultaneous loss of the cbh1 protein coding region, as well as the presence of the designed promoter mutations, were verified by Southern analyses. The transformants in which a single copy of the expression cassette was integrated into the cbh1 locus were chosen for more detailed analyses.

Integration of the construct into an ectopic chromosomal location was far more common than into the cbh1 locus.

CBHI⁻ transformants were obtained at a frequency of about 5%, but the majority of them contained extra copies of the transformed construct. To obtain single copy integrants at the cbh1 locus was not always possible in practice especially for certain constructs. The plate assays revealed that 5–10% of the random integrants, of for instance pMLO 16, produced blue color even in repressing conditions. This could be caused by integration of multiple copies which may for instance titrate out repressor proteins, loss of promoter sequences in the event of recombination leading to derepression, or alternatively by position effects such as chromatin structure at the site of integration. However, the true effects of the promoter alterations were not difficult to assess due to the possibility of rapidly screening dozens of transformants, usually over 40, by the plate assay.

EXAMPLE 3

Expression Using Shortened Promoters

A series of lacZ expression vectors with deletion derivatives of the cbh1 promoter were generated starting from the polylinker at –1497 in pMLO16 and proceeding towards the protein coding region. The deletion variants (FIG. 2) were transformed into Trichoderma. The transformants were βGal⁺ in the X-gal plate assay when grown on cellobiose medium.

A surprising finding was that even the deletion forms retaining only 390–210 bp of the 3' sequences of the cbh1 promoter were able to drive strong expression of lacZ on cellobiose, glucose-fructose, and sorbitol media as shown by the plate assay. Furthermore, increase in βGal expression following addition of sophorose onto sorbitol-grown colonies could be seen. Deletions starting in the middle of the 2.2 kb promoter fragment and extending downstream from –1497 were made, thus including more than 700 bp of the sequences upstream of the deletion point; therefore the possibility remained that these sequences were responsible for the expression. To test this, selected deletion constructs including del5(11) and del7(5), and pMLO16, were digested with restriction enzymes cutting at the polylinker at –1497 and at the 3' end of the cbh1 terminator thus generating expression cassettes without the sequences upstream of –1497 (see FIG. 2). Comparison of random transformants with and without the upstream sequences using the X-gal plate assay gave similar results in each case suggesting that the sequences upstream of –1497 did not affect the regulatory properties of the promoter.

Induction of lacZ expression under two of the deletion promoters, del5(11) that retains 390 bp of the promoter sequences upstream of the translation initiation codon, and del7(5) that retains 210 bp (75 bp upstream of the TATA-box), both with and without the sequences upstream of –1497, were studied in more detail in shake flask cultures on sorbitol medium using sophorose as an inducer. In this experiment, only the transformants 5(11) and pMLO 16 are single copy site specific integrants at the cbh1 locus. Northern analysis showed that lacZ expression from all the constructs was comparable and was increased by sophorose. The result was the same with del7(5) and del5(11). Thus, it can be concluded that the sequences located within the 210 bp region at the 3' end of the cbh1 promoter, present in the construct del7(5), are sufficient for sophorose induction.

To further narrow down the region responsible for the induction, three additional shortened forms of the cbh1 promoter were generated. The constructs were pMI-33, pMI-34 and pMI-35 covering sequences from –1 to –184, to –161, and to –140, respectively (FIG. 2). The host was transformed with BstEII-SphI cut DNA producing expression cassettes lacking sequences upstream of –1497. Expression of lacZ mRNA was studied by Northern analyses (FIG. 2). lacZ expression under the pMI-33; and pMI-34 promoters was occurring on sorbitol medium and was still clearly induced by the addition of sophorose. The same result was seen in the plate assay. As none of these short expression cassettes were integrated into the cbh1 locus, this result further proves that expression of lacZ is independent of sequences upstream of –1497. lacZ expression in the pMI-35 transformants was more variable both in the plate assay and in the Northern analysis (FIG. 3). In two out of the nine clones studied by Northern analysis lacZ was expressed on sorbitol medium at the level comparable with that of pMI-33 and pMI-34 and was induced by sophorose, whereas the remaining seven clones produced lacZ at a very low level and in five of these clones a very weak sophorose induction might have occurred (results of four representative clones shown in FIG. 3).

Sequences mediating sophorose induction lie within the 161 bp situated upstream of the initiator ATG in the cbh1 promoter, either in the 30 bp region 5' of TATA, or in the region downstream of the TATA-box. These sequences seem to be also responsible for the expression observed on cellobiose medium in the plate assays. The shortest promoter derivative studied, covering sequences between –140 (8 bp upstream of the TATA-box) and –1, gave variable results being in some transformants clearly induced by sophorose but in most of them not. It is possible that upon integration of the construct into the chromosome some functionally important nucleotides might be lost or gained, and no definite conclusion can thus be drawn whether the 8 bp adjacent to the TATA-box are involved in sophorose induction.

EXAMPLE 4 cbh1 Promoter—Sequence Homologies

The 6-bp nucleotide sequence 5'GGC(T/A)AA is repeated 15 times in cbh1 promoter of *T. reesei*. One of the repeats is situated between nucleotides –161 and –146 upstream of initiator ATG, within the 29-bp region that is sufficient for sophorose induction in *T. reesei*. The repeats are found in both upper and lower strands. The same sequence is found also in cbh2 (3×), egl1 (2×), xyl1 (3×), egl5 (3×) promoters of *T. reesei*. Furthermore, these sequences are found in cellulase and hemicellulase promoters in other filamentous fungi. These include *Aspergillus tubigiensis* xlnA, *Aspergillus nidulans* xlnC, *Aspergillus niger* xynB, *Aspergillus aculeatus* endoglucanase (FI-CMCase), and *Aspergillus kawachii* xynC. The sequence is not found in the crel promoter of *T. reesei*, or in the glucoamylase (glaA) promoters of *Aspergillus niger* or *Aspergillus oryzae*.

Another sequence element of interest found within the above mentioned region is 5'CGAAT, which is found in glucoamylase (glaA) promoters of *Aspergillus niger* and *Aspergillus oryzae* this sequence was shown to be a part of a region which is responsible for high expression and starch induction (reviewed in MacKenzie, D. A., et al., *J. Gen. Microbiol*. 139: 2295–2307 (1993)). cbh1 promoter sequence in question in bold (just upstream of TATA box) (SEQ ID NO. 7):

–161                 .                 .                 TGAGCTAGTA
    GGCAAAGTCAGCGAATGTGTATATATAAAA . . .

EXAMPLE 5

Transcriptional Activation of HIS Expression through cbh1 Promoter Sequences at –161 to –133 pRS315 (Sikorski, R.S., and Hieter, P., *Genetics* 122:19–27 (1989)), the yeast single-copy vector containing the LEU2 marker, was digested with the restriction enzymes BamHI and SalI. The HIS3 reporter gene of *S. cerevisiae* was cloned from cosmid p3030 (Hohn and Hinnen, unpublished; see Penttilä, M.E., et al., *Mol. Gen. Genet.* 194: 494–499 (1984), incorporated herein by reference) by PCR using the 5'primer AAA <u>GGA TCC</u> TTA TAC ATT ATA TAA AGT AAT G (SEQ ID NO. 19) and the 3'primer ATA TA<u>G TCG AC</u>C TCG GGG ACA CCA AAT ATG G (SEQ ID NO, 20). The underlined GGATCC is a BamHI site and GTCGAC is a SalI site. The PCR fragment was digested with the above mentioned enzymes and ligated to the vector followed by sequencing of the PCR fragment. The HIS3 gene of the resulting pAS1 plasmid contains a minimal promoter, 55 bp upstream from the ATG, which is not able to support growth in a medium lacking histidine. Plasmid pMS95, used as a negative control plasmid, was constructed as follows. pAS1 plasmid was digested with the restriction enzyme SacI. A 1.4 kb SacI-fragment from a non-relevant cDNA (5' end of a glutamate receptor cDNA from rat) was ligated in front of the HIS3 gene. This plasmid was used as a negative control containing no promoter elements, since the polylinker region present in the vector pAS1 caused leakage of the HIS3 gene.

The 29-bp region in cbh1 promoter located between nucleotides –161 and –133 upstream of protein-coding region, which was implicated in the mediation of sophorose induction of the cbh1 promoter in Trichoderma as described in Example 4, is cloned into the negative control plasmid to the BamHI site just upstream of the TATA box. Complementary oligonucleotides 5'<u>GAT CCT</u> GAG CTA GTA GGC AAA GTC AGC GAA TGT GTG AGC TAG TAG GCA AAG TCA GCG AAT GTG TGA GCT AGT AGG CAA AGT CAG CGA ATG TGG (SEQ ID 8) and 5'<u>GAT CCC</u> ACA TTC GCT GAC TTT GCC TAC TAG CTC ACA CAT TCG CTG ACT TTG CCT ACT AGC TCA CAC ATT CGC TGA CTT TGC CTA CTA GCT CAG (SEQ ID 9), covering sequences from –161 to –133 in three copies and BamHI compatible ends (underlined), are synthesized, annealed and ligated to the BamHI cut vector. Oligonucleotides having a random sequence of similar size and overall nucleotide composition 5'<u>GAT CCT</u> GAA GAA TGG GAA GCA TTG CTA AGC GGT GTG AAG AAT GGG AAG CAT TGC TAA GCG GTG TGA AGA ATG GGA AGC ATT GCT AAG CGG TGG(SEQ ID 10) and 5'<u>GAT CCC</u> ACC GCT TAG CAA TGC TTC CCA TTC TTC ACA CCG CTT AGC AAT GCT TCC CAT TCT TCA CAC CGC TTA GCA ATG CTT CCC ATT CTT CAG (SEQ ID 11) are made as controls and cloned into the same vector. The transformants carrying the reporter plasmids do not grow on media lacking histidine. The reporter yeast is transformed with a cDNA library of *T. reesei*, transformant colonies are selected on SC-LEU-URA plates and subsequently screeened for HIS+ phenotype. Plasmids originating from the cDNA library that support growth only in the presence of the reporter plasmid, but not alone or with the negative control plasmid, are obtained. These plasmids carry genes that code for proteins which activate transcription through binding to the cbh1 promoter sequences present in the reporter construct.

EXAMPLE 6

Coordinated Regulation of Cellulase and Hemicellulase Expression

In order to study regulation of expression of genes encoding hemicellulose-degrading enzymes, *T. reesei* QM9414 was grown on minimal medium (Penttilä, M., et al, *Gene* 61: 155–164 (1987) supplemented with different carbon sources. These were sorbitol, sorbitol+sophorose, sorbitol+mannobiose, sorbitol+xylobiose, sorbitol+cellobiose, cellobiose, glycerol, glycerol+mannobiose, glycerol+xylobiose, mannose, xylose, xylitol, arabinose, arabitol, galactose, lactose, Lenzing xylan, methylglucuronoxylan, oat spelts xylan, Solka floc cellulose, beta-glucan, glucose, glucose+sophorose, glucose+mannobiose, and glucose+xylobiose. Total RNA was isolated as described by Chirgwin, J.M. er al., *Biochem. J* 18: 5294–5299 (1979) and analyzed by Northern blotting and hybridized. The following genes were used as probes: cbh1, egl5, bgl1, xyl1, xyl2, bxl1, abf1, glr1, axe1, man1, agl1, agl2, agl3. The filters were washed in once 5×SSPE, twice in 1×SSPE, 0.1% SDS, and twice in 0.1×SSPE, 0.1% SDS at 42° C. for 20 min each wash. Results of the hybridizations are shown in Table 5. The results show common patterns of regulation of genes encoding cellulases and hemicellulases, and regulation of enzymes attacking related substrates is even further coordinated. This suggests that common regulatory proteins regulate the expression of enzymes degrading hemicellulose and cellulose. Promoter sequences of cbh1, egl5, bgl1, xyl1 and xyl2 are available to date. A common sequence element. 5' GGC(T/A)AA is found in cbh1, egl5 and xyl1 promoters raising the possibility that a common regulatory protein may bind to the sequence.

TABLE 2

Expression of hydrolase genes in *T. reesei* cultivated for 3 days** on different carbon sources

| Carbon Source* | Growth | cbh1 | egl5 | bgl1 | xyn1 | xyn2 | bxl1 | abf1 | glr1 | axe1 | man1 | agl1 | agl3 | agl2 |
|---|---|---|---|---|---|---|---|---|---|---|---|---|---|---|
| QM 9414 | | | | | | | | | | | | | | |
| Sorb | + | – | – | – | – | – | – | – | – | – | – | – | – | + |
| Sorb/Soph | + | ++++ | ++++ | + | + | +(+) | ++ | + | – | + | – | + | – | +(+) |
| Sorb/(Man)$_2$ | + | – | – | – | – | – | – | – | – | – | – | + | – | + |
| Sorb/(Xyl)$_2$ | + | – | – | – | – | – | ++ | + | – | – | – | + | – | + |
| Sorb/(Glc)$_2$ | + | +++ | ++ | – | – | – | + | + | – | – | – | ++ | – | +++ |
| (Glc)$_2$ | + | +++ | ++ | – | – | – | + | + | – | – | – | + | – | ++ |
| Glys/(Man)$_2$ | + | – | – | – | – | – | – | – | – | – | – | + | – | + |
| Glys/(Xyl)$_2$ | + | + | – | – | ++ | +++ | ++++ | – | ++ | + | – | + | – | +(+) |
| Glys | + | – | – | – | – | – | – | – | – | – | – | + | – | – |
| Mannose | +++ | – | – | – | – | – | – | – | – | – | – | + | – | – |
| Xylose | +++ | – | – | – | – | – | – | – | – | – | – | – | – | – |
| Xylitol | +++ | – | – | – | – | – | – | + | – | – | – | + | – | + |

TABLE 2-continued

Expression of hydrolase genes in *T. reesei* cultivated for 3 days** on different carbon sources

| Carbon Source* | Growth | cbh1 | egl5 | bgl1 | xyn1 | xyn2 | bxl1 | abf1 | glr1 | axe1 | man1 | agl1 | agl3 | agl2 |
|---|---|---|---|---|---|---|---|---|---|---|---|---|---|---|
| Arabinose | ++ | - | - | - | - | - | + | + | - | - | - | - | - | - |
| Arabitol | ++ | ++ | - | - | ++ | ++ | +++ | ++++ | + | + | - | ++ | - | +++ |
| Galactose | ++ | - | - | - | - | - | - | - | - | ++ | - | +++ | - | ++++ |
| Lactose | + | ++ | ++ | - | - | - | + | - | - | - | - | - | - | - |
| L. Xylan | +++ | - | - | - | ++ | - | ++ | - | + | - | - | - | - | - |
| MeGlc-Xylan | +++ | + | + | - | + | ++ | +(+) | - | (+)? | ++ | - | - | - | - |
| O.S. Xylan | +++ | + | - | - | +++ | + | ++ | +++ | + | - | - | + | - | + |
| Cellulose | +++ | ++++ | ++ | + | ++ | ++ | ++(+) | - | + | +++ | ++ | - | - | + |
| βGlucan | ++ | +++ | ++ | + | - | - | + | + | - | - | + | + | - | + |
| Glc | +++ | - | - | - | - | - | - | - | - | - | - | - | - | - |
| Glc/Soph | +++ | - | - | - | - | - | - | - | - | - | - | - | - | - |
| Glc/(Man)₂ | +++ | - | - | - | - | - | - | - | - | - | - | - | - | - |
| Glc/(Xyl)₂ | +++ | - | - | - | - | - | - | - | - | - | - | - | - | - |
| Glc depl. RutC 30 | +++ | ++++ | +++ | ++ | - | ++ | ++ | +++ | + | ++ | + | +++ | - | +++ |
| Glc | +++ | ++++ | ++(+) | - | + | - | +++ | + | + | + | - | +++ | + | + |

*Glc: glucose, Sorb: sorbitol, Glys: glycerol, Soph: sophorose, (Man)₂: mannobiose, (Xyl)₂: xylobiose, (Glc)₂: cellobiose, MeGlc-Xylan: 4-O-Methylglucouronoxylan, L. Xylan: Lenzin xylan, O.S. Xylan: oat spelt xylan.
**The presence of the carbon source still at the end of the cultivation was verified by HPLC and visually (polymeric substrates).

EXAMPLE 7

DNA mobility shift assays were performed to study if cellular proteins bind to the DNA sequence found immediately upstream of the TATA box of the cbh1 promoter. The fragment to be labeled was made by annealing two oligonucleotides containing the following sequences 5' aattcAT-TAA ACGGAATGAG CTAGTAJGCA AAGTCAGCGA ATGTGt 3'(SEQ ID NO. 12) and 5' ctagaCACAT TCGCT-GACTT TGCCTACTAG CTCATTCCGT TTAATg 3'(SEQ ID NO. 13). The annealed fragment was end labeled with $P^{32}\alpha CTP$ nucleotide by Klenow enzyme.

The unspecific DNA used for competition in the binding reaction was prepared by annealing two oligonucleotides containing the sequences 5'AATTCGATAA AGATAG (CCTC ATTAAACGGA ATGAGCTAGT T 3'(SEQ ID NO.14) and 5' CTAGAACTAG CTCATTCCGT TTAAT-GAGGC TATCTTTATC G 3'(SEQ ID NO. 15).The mycelial total protein lysates were prepared from T. reesei grown in shake flasks on minimal media containing 2% glucose or 1% Avicel cellulose for 20 h and 5 d respectively. Mycelia were harvested from the culture media by filtration trough GF/B glass-microfiber filters (Whatman), washed with buffer A (20 mM Hepes, pH 7.9, 100mMKCl, 2 mM EDTA, 10 mM DTT and 2 mM PMSF) and grounded under liquid nitrogen. The ground mycelia was dissolved in buffer A and incubated on ice for 10 min. The cell debris was spun down and the supernatant was collected and used for mobility shift assays.

The total protein lysate (10 µg) was incubated with the labeled DNA fragment (1 ng, 20 000 CPM) for 30 minutes at 25° C. in a 20µl total volume in a reaction mixture containing 25 mM Hepes, 50 mM NaCl, 10% glycerol, 4 mM spermidine, 5 mM MgCl₂, 2µM ZnCl₂ and 100µg/ml poly (dI•dC). In the competition experiments unlabeled fragments were added to the reaction mixture in 5–100 excess of the labeled fragment. DNA protein complexes were separated on a 6% non-denaturing polyaicrylamide gel containing 10% glycerol in 12.5 mM Tris-borate buffer (pH 8.3), run 12V/cm at 4° C. The gel was dried and autoradiographed. This experiment showed that DNA-binding proteins bind specifically to the DNA fragment studied (FIG. 4).

---

What is claimed is:

1. A promoter, wherein said promoter comprises the nucleotide sequence contained in the region located between and including the nucleotides −184 and −1 (SEQ ID NO:16), −161 and −1 (SEQ ID NO:17), −140 and −1 (SEQ ID NO:18), or −161 and −133 (SEQ ID NO:2) upstream of the protein-coding region of the *T. reesei* cbh1 gene, wherein the length of said promoter is less than 500 nucleotides and wherein said promoter is inducible by sophorose.

2. The promoter of claim 1, wherein the length of said promoter is less than 210 nucleotides.

3. The promoter of claim 1, wherein said nucleotide sequence is that contained in the region between and including the nucleotides −184 and −1 (SEQ ID NO:16).

4. The promoter of claim 1, wherein said nucleotide sequence is that contained in the region between and including the nucleotides −161 and −1 (SEQ ID NO:17).

5. The promoter of claim 1, wherein said nucleotide sequence is that contained in the region between and including the nucleotides −140 and −1 (SEQ ID NO:18).

6. The promoter of claim 1, wherein said nucleotide sequence is that contained in the region between and including the nucleotides −161 and −133 (SEQ ID NO:2).

7. The promoter of claim 1, wherein said promoter is a hydrolytic enzyme promoter.

8. The promoter of claim 1, wherein said promoter is a cellulase or hemicellulase promoter.

9. The promoter of claim 1, wherein said promoter is not repressible by glucose.

10. The promoter of claim 1, wherein said promoter lacks *T. reesei* cbh1 promoter sequences above position −184.

11. The promoter of claim 1, wherein said promoter lacks *T. reesei* cbh1 promoter sequences above position −161.

12. The promoter of claim 1, wherein said promoter lacks *T. reesei* cbh1 promoter sequences above position −140.

13. The promoter of claim 1, wherein said promoter lacks *T. reesei* cbh1 promoter sequences above position −161 and below position −133.

14. The promoter of claim 1, wherein said promoter comprises the following sequence 5' GGC(T/A)AA 3'.

15. The promoter of claim 1, wherein said promoter is operably linked to a desired nucleotide sequence that is to be expressed under the control of said promoter.

16. The promoter of any one of claims 14, wherein said promoter is a purified promoter.

17. A vector comprising the promoter of any one of claims 1–15.

18. A host cell comprising the vector of claim 17.

19. A host cell comprising the promoter of any one of claims 1–15.

20. The host cell of claim 19, further comprising a DNA sequence or DNA sequences encoding a protein or proteins regulating transcription of genetic sequences through the presence of said promoter.

21. The host cell of claim 19, wherein said host cell is a filamentous fungus.

22. The host cell of claim 19, wherein said filamentous fungus is Trichodera.

23. The host cell of claim 22, wherein said Trichoderma is selected from the group consisting of *T. reesei, T. harzianum, T. longibrachiatum, T. viride,* and *T. koningii.*

24. The host cell of claim 23, wherein said Trichoderma is *T.reesei.*

25. A method of making a protein in a filamentous fungus, said method comprising expressing a protein under the direction of the promoter of any one of claims 1–15.

26. A method of making a protein in a filamentous fungus, said method comprising expressing a protein under the direction of the promoter of any one of claims 1–15 and simultaneously expressing in said fungus a DNA sequence or DNA sequences encoding a protein regulating transcription of genetic sequences through the presence of said promoter.

* * * * *

UNITED STATES PATENT AND TRADEMARK OFFICE
CERTIFICATE OF CORRECTION

| | | |
|---|---|---|
| PATENT NO. | : 6,001,595 | Page 1 of 1 |
| APPLICATION NO. | : 09/066597 | |
| DATED | : December 14, 1999 | |
| INVENTOR(S) | : Ilmén et al. | |

It is certified that error appears in the above-identified patent and that said Letters Patent is hereby corrected as shown below:

On the title page: Column 1, line 3 of item [54] ("Title"), before "Promoters", please insert --New--.

Column 39, line 45, at claim 1, please delete "cbh1" and insert therein --*cbh1*--.

Column 40, line 40, at claim 10, please delete "cbh1" and insert therein --*cbh1*--.

Column 40, line 42, at claim 11, please delete "cbh1" and insert therein --*cbh1*--.

Column 40, line 44 at claim 12, please delete "cbh1" and insert therein --*cbh1*--.

Column 40, line 46, at claim 13, please delete "cbh1" and insert therein --*cbh1*--.

Column 40, line 53, at claim 16, please delete "14" and insert therein --1-14--.

Column 40, line 66, at claim 22, please delete "19" and insert therein --21-- and at line 67, please delete "Trichodera" and insert therein --*Trichoderma*--.

Column 41, line 1, at claim 23, please delete "Trichoderma" and insert therein --*Trichoderma*--.

Column 41, line 4, at claim 24, please delete "Trichoderma" and insert therein --*Trichoderma*--.

Signed and Sealed this

Third Day of October, 2006

JON W. DUDAS
*Director of the United States Patent and Trademark Office*